(12) United States Patent
Kim

(10) Patent No.: US 11,708,611 B2
(45) Date of Patent: Jul. 25, 2023

(54) METHOD FOR DIAGNOSING PROSTATIC DISEASE VIA BACTERIAL METAGENOMIC ANALYSIS

(71) Applicant: MD HEALTHCARE INC., Seoul (KR)

(72) Inventor: Yoon-Keun Kim, Namyangju-si (KR)

(73) Assignee: MD HEALTHCARE INC., Seoul (KR)

( * ) Notice: Subject to any disclaimer, the term of this patent is extended or adjusted under 35 U.S.C. 154(b) by 602 days.

(21) Appl. No.: 16/474,543

(22) PCT Filed: Dec. 27, 2017

(86) PCT No.: PCT/KR2017/015576
§ 371 (c)(1),
(2) Date: Jun. 27, 2019

(87) PCT Pub. No.: WO2018/124742
PCT Pub. Date: Jul. 5, 2018

(65) Prior Publication Data
US 2022/0259663 A1 Aug. 18, 2022

(30) Foreign Application Priority Data

Dec. 28, 2016 (KR) .................. 10-2016-0181570
Dec. 26, 2017 (KR) .................. 10-2017-0180014

(51) Int. Cl.
*C12Q 1/6886* (2018.01)
*C12Q 1/6806* (2018.01)
*C12Q 1/6869* (2018.01)

(52) U.S. Cl.
CPC ......... *C12Q 1/6886* (2013.01); *C12Q 1/6806* (2013.01); *C12Q 1/6869* (2013.01); *C12Q 2600/112* (2013.01)

(58) Field of Classification Search
None
See application file for complete search history.

(56) References Cited

U.S. PATENT DOCUMENTS

2018/0195111 A1* 7/2018 Gosiewski ........... C12Q 1/6869

FOREIGN PATENT DOCUMENTS

| CN | 102084000 A | 6/2011 |
|----|-------------|--------|
| CN | 111094596 A | 5/2020 |
| JP | 2013503857 A | 2/2013 |
| JP | 2013503858 A | 2/2013 |
| KR | 10-2011-0025603 A | 3/2011 |
| KR | 10-2011-0073049 A | 6/2011 |
| KR | 10-2016-0073157 A | 6/2016 |
| WO | 2009100029 A1 | 8/2009 |
| WO | 2016085356 A1 | 6/2016 |
| WO | 2016099076 A1 | 6/2016 |
| WO | WO-2017009693 A1 * | 1/2017 ............ C12Q 1/686 |
| WO | 2019004668 A1 | 1/2019 |

OTHER PUBLICATIONS

Miranda et al. PLoS ONE. May 2014. 9(5): e96094) (Year: 2014).*
Illumina (16S Metagenomic Sequencing Library Preparation. Nov. 27, 2013. p. 1-28, available via URL: <support.illumina.com/content/dam/illumina-support/documents/documentation/chemistry_documentation/16s/16s-metagenomic-library-prep-guide-15044223-b.pdf> (Year: 2013).*
Yu et al., "Urinary microbiota in patients with prostate cancer and benign prostatic hyperplasia", Arch Med Sci, 2015, vol. 11, No. 2, pp. 385-394.
Smelov et al., "Metagenomic Sequencing of Expressed Prostate Secretions", Journal of Medical Virology, 2014, vol. 86, No. 12, pp. 2042-2048.
Park et al., "Prostate-specific extracellular vesicles as a novel biomarker in human prostate cancer", Scientific Reports, 2016, vol. 6, 30386, pp. 1-8.
International Search Report for Corresponding international Application No. PCT/KR2017/015576 (2 Pages) (dated Apr. 10, 2018).
Office Action dated Nov. 2, 2022 for the corresponding Chinese Patent Application No. 201780081402.0, 16 pages.
Barreiro, Karina et al., "Urinary extracellular vesicles. A promising shortcut to novel biomarker discoveries", Cell and Tissue Research, Springer, DE, Apr. 20, 2017, , pp. 217-227,vol. 369, No. I, ISSN: 0302-766X.
Lee, Kevin C. et al., "Niche Filtering of Bacteria in Soil and Rock Habitats of the Colorado Plateau Desert, Utah, USA", Frontiers in Microbiology, Sep. 26, 2016, vol. 7, article 1489.
Sandri et al., "Raw meat based diet influences faecal microbiome and end products of fermentation in healthy dogs", BMC Veterinary Research, 2017, 13:65.
Yoo, Jae Young et al., "16S rRNA gene-based metagenomic analysis reveals differences in bacteria-derived extracellular vesicles in the urine of pregnant and non-pregnant women", Experimental & Molecular Medicine, 2016, vol. 48, e208.

* cited by examiner

*Primary Examiner* — Carla J Myers
(74) *Attorney, Agent, or Firm* — Vorys, Sater, Seymour and Pease LLP; Mih Suhn Koh

(57) ABSTRACT

A method of diagnosing prostatic diseases such as prostate cancer, prostatic hyperplasia, and the like through bacterial metagenomic analysis, and more particularly, to a method of diagnosing prostate cancer or prostatic hyperplasia by analyzing an increase or decrease in content of extracellular vesicles derived from specific bacteria through bacterial metagenomic analysis using a subject-derived sample. An extracellular vesicle secreted from a bacterium present in the environment can be absorbed into the body and directly affect the occurrence of inflammation and cancer, and prostatic diseases such as prostate cancer, prostatic hyperplasia, and the like is difficult to diagnose early on before any symptom appears, which makes efficient treatment difficult. As such, through the metagenomic analysis on a gene present in a bacterium-derived extracellular vesicle using a human body-derived sample according to the present invention, the risk of the onset of prostate cancer and prostatic hyperplasia can be predicted in advance.

1 Claim, 17 Drawing Sheets

Specification includes a Sequence Listing.

SEQUENCE LISTING

<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: n is G or A or T or C

<400> SEQUENCE: 1
tcgtcggcag cgtcagatgt gtataagaga cagcctacgg gnggcwgcag         50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc    55

METHOD FOR DIAGNOSING PROSTATIC DISEASE VIA BACTERIAL METAGENOMIC ANALYSIS

CROSS-REFERENCE TO RELATED APPLICATIONS

This application is a 371 of PCT/KR2017/015576, filed Dec. 27, 2017, which claims the benefit of priority from Korean Patent Application No. 10-2016-0181570, filed Dec. 28, 2016 and Korean Patent Application No. 10-2017-0180014, filed Dec. 26, 2017, the contents of each of which are incorporated herein by reference in its entirety.

STATEMENT ABOUT SEQUENCE LISTING

The Computer Readable Form (CRF) of Sequence Listing is hereby incorporated by reference.

TECHNICAL FIELD OF THE INVENTION

The present invention relates to a method of diagnosing prostatic diseases such as prostate cancer, prostatic hyperplasia, and the like through bacterial metagenomic analysis, and more particularly, to a method of diagnosing a prostatic disease by analyzing an increase or decrease in content of extracellular vesicles derived from specific bacteria through bacterial metagenomic analysis using a subject-derived sample.

BACKGROUND OF THE INVENTION

The prostate gland, which is a part of the male reproductive organ, is an organ that produces a liquid for producing semen by mixing with sperm. Prostatic hyperplasia is a condition in which the prostate gland is enlarged, thus blocking a path through which urine in a lower site of the bladder is discharged, resulting in blocking of or a decrease in urinary flow of the urethra, and benign prostatic hyperplasia (BPH), which is a male urination disorder, is a disease causing difficulty in urination due to enlargement of the prostate gland. The prostate gland surrounds a tube (urethra) through which urine is transferred from the bladder and expands evenly during puberty, and with age, BPH progresses by concentrating on the urethral lateral part of the gland. The cause of benign prostatic hyperplasia has not yet been clearly discovered, but it is known that various factors act as in other chronic diseases. Since the prostate gland is a male hormone-dependent organ, a male hormone is continuously required to maintain growth and functions, and when the male hormone is not produced by castration, the prostate gland contracts, and it is known that prostate hyperplasia is associated with genetic factors, family history, and the like.

Prostate carcinoma is a malignant tumor that develops in the prostate gland, and in most cases, is adenocarcinoma (cancer of gland cells) that occurs in prostate cells. Risk factors for prostate cancer rapidly increase at an older age (50 years old or older). According to race, Asian people have the lowest incidence rate, and genetic predisposition, family history, male hormones, diabetes, obesity, westernized diet (increase in intake of animal fat), infection, and the like are known as risk factors. Although there is no clear evidence that early medical checkups can prevent death due to prostate cancer, it is generally recommended that males at an age of 50 years old or more who are expected to have a life expectancy of more than 10 years receive a blood (serum) prostate-specific antigen (PSA) test and digital rectal examination every year. However, despite much progress in modern Western medicine, there is still no method of predicting prostate cancer using a non-invasive method, and there are many cases in which solid cancers such as prostate cancer and the like are detected after development using existing diagnosis methods. Thus, it is effective to provide a method of preventing the onset of prostate cancer in a high risk group by predicting the onset and causative factor of prostate cancer to reduce medical costs and prevent death due to prostate cancer.

Meanwhile, it is known that the number of microorganisms symbiotically living in the human body is 100 trillion which is 10 times the number of human cells, and the number of genes of microorganisms exceeds 100 times the number of human genes. A microbiota or microbiome is a microbial community that includes bacteria, archaea, and eukaryotes present in a given habitat. The intestinal microbiota is known to play a vital role in human's physiological phenomena and significantly affect human health and diseases through interactions with human cells. Bacteria coexisting in human bodies secrete nanometer-sized vesicles to exchange information about genes, proteins, and the like with other cells. The mucous membranes form a physical barrier membrane that does not allow particles with the size of 200 nm or more to pass therethrough, and thus bacteria symbiotically living in the mucous membranes are unable to pass therethrough, but bacteria-derived extracellular vesicles have a size of approximately 100 nm or less and thus relatively freely pass through the mucous membranes and are absorbed into the human body.

Metagenomics, also called environmental genomics, may be analytics for metagenomic data obtained from samples collected from the environment (Korean Patent Publication No. 2011-0073049). Recently, the bacterial composition of human microbiota has been listed using a method based on 16s ribosomal RNA (16s rRNA) base sequences, and 16s rDNA base sequences, which are genes of 16s ribosomal RNA, are analyzed using a next generation sequencing (NGS) platform. However, in the onset of prostatic diseases such as prostatic hyperplasia, prostate cancer and the like, identification of causative factors of prostatic diseases through metagenomic analysis of bacteria-derived vesicles isolated from a human-derived substance, such as urine or the like, and a method of diagnosing a risk of developing prostatic diseases have never been reported.

To diagnose a prostatic disease based on causative factors of prostatic hyperplasia and prostate cancer, the inventors of the present invention extracted DNA from bacteria-derived extracellular vesicles in urine, which is a subject-derived sample, and performed metagenomic analysis on the extracted DNA, and, as a result, identified bacteria-derived extracellular vesicles capable of acting as causative factors of prostatic diseases such as prostate cancer, prostatic hyperplasia, and the like, thus completing the present invention based on these findings.

Therefore, an object of the present invention is to provide a method of providing information for prostate cancer diagnosis through metagenomic analysis of bacteria-derived extracellular vesicles. It is another object of the present invention is to provide a method of providing information for prostate cancer diagnosis in prostatic hyperplasia patients through metagenomic analysis of bacteria-derived extracellular vesicles. It is another object of the present invention to provide a method of providing information for prostatic hyperplasia diagnosis through metagenomic analysis of bacteria-derived extracellular vesicles.

However, the technical goals of the present invention are not limited to the aforementioned goals, and other unmentioned technical goals will be clearly understood by those of ordinary skill in the art from the following description.

SUMMARY OF THE INVENTION

To achieve the above-described objects of the present invention, the present invention provides a method of providing information for prostatic disease diagnosis, comprising the following processes:

(a) extracting DNA from extracellular vesicles isolated from a subject sample;

(b) performing polymerase chain reaction (PCR) on the extracted DNA using a pair of primers having SEQ ID NO: 1 and SEQ ID NO: 2; and (c) comparing an increase or decrease in content of bacteria-derived extracellular vesicles between a normal individual-derived sample and a prostate cancer patient-derived sample through sequencing of a product of the PCR, comparing an increase or decrease in content of bacteria-derived extracellular vesicles between a prostatic hyperplasia patient-derived sample and a prostate cancer patient-derived sample through sequencing of a product of the PCR, or comparing an increase or decrease in content of bacteria-derived extracellular vesicles between a normal individual-derived sample and a prostatic hyperplasia patient-derived sample through sequencing of a product of the PCR.

The present invention also provides a method of diagnosing prostatic disease diagnosis, comprising the following processes:

(a) extracting DNA from extracellular vesicles isolated from a subject sample;

(b) performing polymerase chain reaction (PCR) on the extracted DNA using a pair of primers having SEQ ID NO: 1 and SEQ ID NO: 2; and (c) comparing an increase or decrease in content of bacteria-derived extracellular vesicles between a normal individual-derived sample and a prostate cancer patient-derived sample through sequencing of a product of the PCR, comparing an increase or decrease in content of bacteria-derived extracellular vesicles between a prostatic hyperplasia patient-derived sample and a prostate cancer patient-derived sample through sequencing of a product of the PCR, or comparing an increase or decrease in content of bacteria-derived extracellular vesicles between a normal individual-derived sample and a prostatic hyperplasia patient-derived sample through sequencing of a product of the PCR.

The present invention also provides a method of predicting a risk for prostatic disease, comprising the following processes:

(a) extracting DNA from extracellular vesicles isolated from a subject sample;

(b) performing polymerase chain reaction (PCR) on the extracted DNA using a pair of primers having SEQ ID NO: 1 and SEQ ID NO: 2; and (c) comparing an increase or decrease in content of bacteria-derived extracellular vesicles between a normal individual-derived sample and a prostate cancer patient-derived sample through sequencing of a product of the PCR, comparing an increase or decrease in content of bacteria-derived extracellular vesicles between a prostatic hyperplasia patient-derived sample and a prostate cancer patient-derived sample through sequencing of a product of the PCR, or comparing an increase or decrease in content of bacteria-derived extracellular vesicles between a normal individual-derived sample and a prostatic hyperplasia patient-derived sample through sequencing of a product of the PCR.

In one embodiment of the present invention, in process (c), prostate cancer may be diagnosed by comparing an increase or decrease in content of extracellular vesicles derived from one or more bacteria selected from the group consisting of the phylum Tenericutes, the phylum Euryarchaeota, the phylum Verrucomicrobia, the phylum Gemmatimonadetes, the phylum Acidobacteria, and the phylum Planctomycetes of the subject sample with that of a normal individual-derived sample.

In one embodiment of the present invention, in process (c), prostate cancer may be diagnosed by comparing an increase or decrease in content of extracellular vesicles derived from one or more bacteria selected from the group consisting of the class Mollicutes, the class Methanobacteria, the class Verrucomicrobiae, the class Acidimicrobiia, the class Spartobacteria, the class Acidobacteria-6, the class Gemmatimonadetes, the class Acidobacteriia, and the class Pedosphaerae of the subject sample with that of a normal individual-derived sample.

In one embodiment of the present invention, in process (c), prostate cancer may be diagnosed by comparing an increase or decrease in content of extracellular vesicles derived from one or more bacteria selected from the group consisting of the order Stramenopiles, the order Alteromonadales, the order RF39, the order Rickettsiales, the order Neisseriales, the order Methanobacteriales, the order Verrucomicrobiales, the order Myxococcales, the order Acidimicrobiales, the order Chthoniobacterales, the order iii1-15, the order Acidobacteriales, the order Ellin329, and the order Pedosphaerales of the subject sample with that of a normal individual-derived sample.

In another embodiment of the present invention, in process (c), prostate cancer may be diagnosed by comparing an increase or decrease in content of extracellular vesicles derived from one or more bacteria selected from the group consisting of the family Peptococcaceae, the family Exiguobacteraceae, the family Actinomycetaceae, the family Cellulomonadaceae, the family Mitochondria, the family Fusobacteriaceae, the family S24-7, the family Porphyromonadaceae, the family Flavobacteriaceae, the family Moraxellaceae, the family Neisseriaceae, the family Methanobacteriaceae, the family Verrucomicrobiaceae, the family Rikenellaceae, the family Weeksellaceae, the family Streptomycetaceae, the family Helicobacteraceae, the family Chthoniobacteraceae, and the family Koribacteraceae of the subject sample with that of a normal individual-derived sample.

In another embodiment of the present invention, in process (c), prostate cancer may be diagnosed by comparing an increase or decrease in content of extracellular vesicles derived from one or more bacteria selected from the group consisting of the genus *Rhizobium*, the genus *Tetragenococcus*, the genus *Proteus*, the genus *Morganella*, the genus *Exiguobacterium*, the genus *Oribacterium*, the genus *Porphyromonas*, the genus *Actinomyces*, the genus *Cellulomonas*, the genus *Jeotgalicoccus*, the genus *Acinetobacter*, the genus *Fusobacterium*, the genus *Enterobacter*, the genus *Neisseria*, the genus *Adlercreutzia*, the genus SMB53, the genus *Parabacteroides*, the genus *Faecalibacterium*, the genus *Catenibacterium*, the genus *Roseburia*, the genus *Akkermansia*, the genus *Methanobrevibacter*, the genus *Clostridium*, the genus *Klebsiella*, the genus *Chryseobacterium*, the genus *Halomonas*, the genus *Aggregatibacter*, the genus *Rhodoplanes*, the genus *Thermoanaerobacterium*, the genus *Candidatus Koribacter*, and the genus *Flexispira* of the subject sample with that of a normal individual-derived sample.

In another embodiment of the present invention, in process (c), prostate cancer may be diagnosed by comparing an increase or decrease in content of extracellular vesicles derived from the bacteria belonging to the phylum Verrucomicrobia of the subject sample with that of a prostatic hyperplasia patient-derived sample.

In another embodiment of the present invention, in process (c), prostate cancer may be diagnosed by comparing an increase or decrease in content of extracellular vesicles derived from one or more bacteria selected from the group consisting of the class Verrucomicrobiae, the class Acidimicrobiia, the class Saprospirae, and the class Pedosphaerae of the subject sample with that of a prostatic hyperplasia patient-derived sample.

In another embodiment of the present invention, in process (c), prostate cancer may be diagnosed by comparing an increase or decrease in content of extracellular vesicles derived from one or more bacteria selected from the group consisting of the order Verrucomicrobiales, the order Acidimicrobiales, the order Saprospirales, the order Pedosphaerales, and the order Ellin329 of the subject sample with that of a prostatic hyperplasia patient-derived sample.

In another embodiment of the present invention, in process (c), prostate cancer may be diagnosed by comparing an increase or decrease in content of extracellular vesicles derived from one or more bacteria selected from the group consisting of the family Verrucomicrobiaceae, the family Chitinophagaceae, and the family Helicobacteraceae of the subject sample with that of a prostatic hyperplasia patient-derived sample.

In another embodiment of the present invention, in process (c), prostate cancer may be diagnosed by comparing an increase or decrease in content of extracellular vesicles derived from one or more bacteria selected from the group consisting of the genus *Ruminococcus*, the genus *Akkermansia*, and the genus *Flexispira* of the subject sample with that of a prostatic hyperplasia patient-derived sample.

In another embodiment of the present invention, in process (c), prostatic hyperplasia may be diagnosed by comparing an increase or decrease in content of extracellular vesicles derived from one or more bacteria selected from the group consisting of the phylum Euryarchaeota and the phylum Acidobacteria of the subject sample with that of a normal individual-derived sample.

In another embodiment of the present invention, in process (c), prostatic hyperplasia may be diagnosed by comparing an increase or decrease in content of extracellular vesicles derived from one or more bacteria selected from the group consisting of the class Methanobacteria, the class Acidobacteria, and the class Acidobacteriia of the subject sample with that of a normal individual-derived sample.

In another embodiment of the present invention, in process (c), prostatic hyperplasia may be diagnosed by comparing an increase or decrease in content of extracellular vesicles derived from one or more bacteria selected from the group consisting of the order Stramenopiles, the order RF39, the order Saprospirales, the order Pseudomonadales, the order Methanobacteriales, and the order Acidobacteriales of the subject sample with that of a normal individual-derived sample.

In another embodiment of the present invention, in process (c), prostatic hyperplasia may be diagnosed by comparing an increase or decrease in content of extracellular vesicles derived from one or more bacteria selected from the group consisting of the family Exiguobacteraceae, the family Flavobacteriaceae, the family Actinomycetaceae, the family Moraxellaceae, the family Ruminococcaceae, the family Rikenellaceae, the family Methanobacteriaceae, and the family Koribacteraceae of the subject sample with that of a normal individual-derived sample.

In another embodiment of the present invention, in process (c), prostatic hyperplasia may be diagnosed by comparing an increase or decrease in content of extracellular vesicles derived from one or more bacteria selected from the group consisting of the genus *Rhizobium*, the genus *Proteus*, the genus *Acinetobacter*, the genus SMB53, the genus *Halomonas*, the genus *Ruminococcus*, the genus *Faecalibacterium*, the genus *Klebsiella*, the genus *Roseburia*, the genus *Leuconostoc*, the genus *Bilophila*, the genus *Chromohalobacter*, and the genus *Methanobrevibacter* of the subject sample with that of a normal individual-derived sample.

In another embodiment of the present invention, the sample may be urine.

Extracellular vesicles secreted from bacteria present in the environment are absorbed into the human body, and thus may directly affect the occurrence of cancer, and it is difficult to diagnose prostatic hyperplasia and prostate cancer early before symptoms occur, and thus efficient treatment therefor is difficult. Thus, according to the present invention, a risk of developing prostatic diseases such as prostatic hyperplasia, prostate cancer, and the like can be predicted through metagenomic analysis of bacteria or bacteria-derived extracellular vesicles by using a human body-derived sample, and thus the onset of prostatic disease can be delayed or prostatic disease can be prevented through appropriate management by early diagnosis and prediction of a risk group for prostatic disease, and, even after prostatic disease occur, early diagnosis for prostatic disease can be implemented, thereby lowering the incidence rate of prostatic disease and increasing therapeutic effects. In addition, patients diagnosed with prostatic hyperplasia or prostate cancer can avoid exposure to causative factors predicted by metagenomic analysis, whereby the progression of prostatic hyperplasia and prostate cancer can be ameliorated, or recurrence thereof can be prevented.

BRIEF DESCRIPTION OF THE DRAWINGS

FIG. 1A illustrates images showing the distribution pattern of intestinal bacteria and EVs derived from bacteria per time (0 h, 5 min, 3 h, 6 h, and 12 h) after being orally administered to mice. FIG. 1B illustrates images showing the distribution pattern of gut bacteria and EVs derived from bacteria after being orally administered to mice and, after 12 hours, blood and various organs (heart, lung, liver, kidney, spleen, adipose tissue, and muscle) of the mice were extracted.

DETAILED DESCRIPTION OF THE INVENTION

Figure 1A:
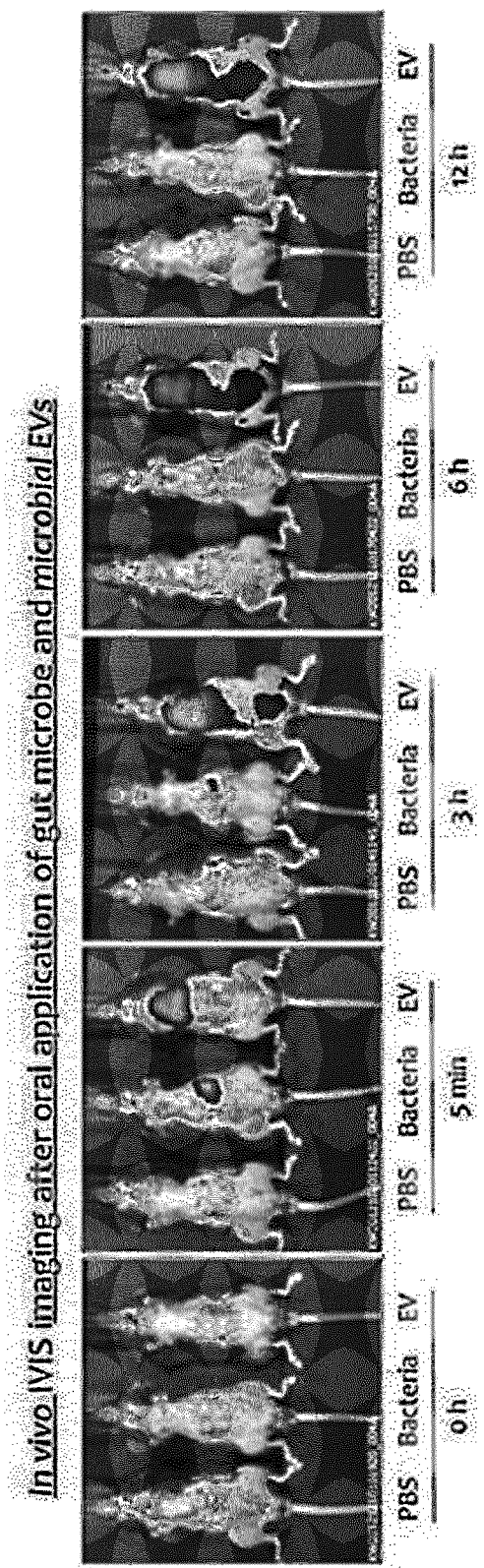
FIGS. 1A and 1B are views for evaluating the distribution pattern of extracellular vesicles (EVs) derived from bacteria in vivo.

The present invention relates to a method of diagnosing prostatic diseases such as prostatic hyperplasia, prostate cancer, and the like through bacterial metagenomic analysis. The inventors of the present invention extracted genes from bacteria-derived extracellular vesicles using a subject-derived sample, performed metagenomic analysis thereon, and identified bacteria-derived extracellular vesicles capable of acting as causative factors of prostatic diseases.

Thus, the present invention provides a method of providing information for prostatic disease diagnosis, comprising the following processes:

(a) extracting DNA from extracellular vesicles isolated from a subject sample;

(b) performing polymerase chain reaction (PCR) on the extracted DNA using a pair of primers having SEQ ID NO: 1 and SEQ ID NO: 2; and (c) comparing an increase or decrease in content of bacteria-derived extracellular vesicles between a normal individual-derived sample and a prostate cancer patient-derived sample through sequencing of a product of the PCR, comparing an increase or decrease in content of bacteria-derived extracellular vesicles between a prostatic hyperplasia patient-derived sample and a prostate cancer patient-derived sample through sequencing of a product of the PCR, or comparing an increase or decrease in content of bacteria-derived extracellular vesicles between a normal individual-derived sample and a prostatic hyperplasia patient-derived sample through sequencing of a product of the PCR.

The term "prostate cancer diagnosis" as used herein refers to determining whether a patient has a risk for prostate cancer, whether the risk for prostate cancer is relatively high, or whether prostate cancer has already occurred. The method of the present invention may be used to delay the onset of prostate cancer through special and appropriate care for a specific patient, which is a patient having a high risk for prostate cancer or prevent the onset of prostate cancer. In addition, the method may be clinically used to determine treatment by selecting the most appropriate treatment method through early diagnosis of prostate cancer.

The term "prostatic hyperplasia diagnosis" as used herein refers to determining whether a patient has a risk for prostatic hyperplasia, whether the risk for prostatic hyperplasia is relatively high, or whether prostatic hyperplasia has already occurred. The method of the present invention may be used to delay the onset of prostatic hyperplasia through special and appropriate care for a specific patient, which is a patient having a high risk for prostatic hyperplasia or prevent the onset of prostatic hyperplasia. In addition, the method may be clinically used to determine treatment by selecting the most appropriate treatment method through early diagnosis of prostatic hyperplasia.

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at once using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as existing one species functionally interact with each other to form a complete species. Technically, it is the subject of techniques that analyzes all DNAs and RNAs regardless of species in one environment using rapid sequencing to identify all species in one environment and verify interactions and metabolism. In the present invention, bacterial metagenomic analysis is performed using bacteria-derived extracellular vesicles isolated from, for example, serum.

In an embodiment of the present invention, metagenomic analysis was performed on genes present in bacteria-derived extracellular vesicles in urine samples of normal individuals, prostatic hyperplasia patients, and prostate cancer patients, and bacteria-derived extracellular vesicles capable of acting as causes of the onset of prostate cancer and prostatic hyperplasia were actually identified by analysis at phylum, class, order, family, and genus levels.

More particularly, in one embodiment of the present invention, as a result of performing metagenomic analysis on bacteria-derived extracellular vesicles at a phylum level, the content of extracellular vesicles derived from bacteria belonging to the phylum Tenericutes, the phylum Euryarchaeota, the phylum Verrucomicrobia, the phylum Gemmatimonadetes, the phylum Acidobacteria, and the phylum Planctomycetes was significantly different between prostate cancer patients and normal individuals (see Example 4).

More particularly, in one embodiment of the present invention, as a result of performing metagenomic analysis on bacteria-derived extracellular vesicles at a class level, the content of extracellular vesicles derived from bacteria belonging to the class Mollicutes, the class Methanobacteria, the class Verrucomicrobiae, the class Acidimicrobiia, the class Spartobacteria, the class Acidobacteria-6, the class Gemmatimonadetes, the class Acidobacteriia, and the class Pedosphaerae was significantly different between prostate cancer patients and normal individuals (see Example 4).

More particularly, in one embodiment of the present invention, as a result of performing metagenomic analysis on bacteria-derived extracellular vesicles at an order level, the content of extracellular vesicles derived from bacteria belonging to the order Stramenopiles, the order Alteromonadales, the order RF39, the order Rickettsiales, the order Neisseriales, the order Methanobacteriales, the order Verrucomicrobiales, the order Myxococcales, the order Acidimicrobiales, the order Chthoniobacterales, the order iii1-15, the order Acidobacteriales, the order Ellin329, and the order Pedosphaerales was significantly different between prostate cancer patients and normal individuals (see Example 4).

More particularly, in one embodiment of the present invention, as a result of performing metagenomic analysis on bacteria-derived extracellular vesicles at a family level, the content of extracellular vesicles derived from bacteria belonging to the family Peptococcaceae, the family Exiguobacteraceae, the family Actinomycetaceae, the family Cellulomonadaceae, the family Mitochondria, the family Fusobacteriaceae, the family S24-7, the family Porphyromonadaceae, the family Flavobacteriaceae, the family Moraxellaceae, the family Neisseriaceae, the family Methanobacteriaceae, the family Verrucomicrobiaceae, the family Rikenellaceae, the family Weeksellaceae, the family Streptomycetaceae, the family Helicobacteraceae, the family Chthoniobacteraceae, and the family Koribacteraceae was significantly different between prostate cancer patients and normal individuals (see Example 4).

More particularly, in one embodiment of the present invention, as a result of performing metagenomic analysis on bacteria-derived extracellular vesicles at a genus level, the content of extracellular vesicles derived from bacteria belonging to the genus *Rhizobium*, the genus *Tetragenococcus*, the genus *Proteus*, the genus *Morganella*, the genus *Exiguobacterium*, the genus *Oribacterium*, the genus *Porphyromonas*, the genus *Actinomyces*, the genus *Cellulomonas*, the genus *Jeotgalicoccus*, the genus *Acinetobacter*, the genus *Fusobacterium*, the genus *Enterobacter*, the genus *Neisseria*, the genus *Adlercreutzia*, the genus SMB53, the genus *Parabacteroides*, the genus *Faecalibacterium*, the genus *Catenibacterium*, the genus *Roseburia*, the genus *Akkermansia*, the genus *Methanobrevibacter*, the genus *Clostridium*, the genus *Klebsiella*, the genus *Chryseobacterium*, the genus *Halomonas*, the genus *Aggregatibacter*, the genus *Rhodoplanes*, the genus *Thermoanaerobacterium*, the genus *Candidatus Koribacter*, and the genus *Flexispira* was significantly different between prostate cancer patients and normal individuals (see Example 4).

In another embodiment of the present invention, metagenomic analysis was performed on bacteria-derived extracellular vesicles in urine samples of prostatic hyperplasia patients and prostate cancer patients, and bacteria-derived extracellular vesicles capable of acting as causes of the onset of prostate cancer in prostatic hyperplasia patients were identified by analysis at phylum, class, order, family, and genus levels.

More particularly, in one embodiment of the present invention, as a result of performing metagenomic analysis on bacteria-derived extracellular vesicles at a phylum level, the content of extracellular vesicles derived from bacteria belonging to the phylum Verrucomicrobia was significantly different between prostate cancer patients and prostatic hyperplasia patients (see Example 5).

More particularly, in one embodiment of the present invention, as a result of performing metagenomic analysis on bacteria-derived extracellular vesicles at a class level, the content of extracellular vesicles derived from bacteria belonging to the class Verrucomicrobiae, the class Acidimicrobiia, the class Saprospirae, and the class Pedosphaerae was significantly different between prostate cancer patients and prostatic hyperplasia patients (see Example 5).

More particularly, in one embodiment of the present invention, as a result of performing metagenomic analysis on bacteria-derived extracellular vesicles at an order level, the content of extracellular vesicles derived from bacteria belonging to the order Verrucomicrobiales, the order Acidimicrobiales, the order Saprospirales, the order Pedosphaerales, and the order Ellin329 was significantly different between prostate cancer patients and prostatic hyperplasia patients (see Example 5).

More particularly, in one embodiment of the present invention, as a result of performing metagenomic analysis on bacteria-derived extracellular vesicles at a family level, the content of extracellular vesicles derived from bacteria belonging to the family Verrucomicrobiaceae, the family Chitinophagaceae, and the family Helicobacteraceae was significantly different between prostate cancer patients and prostatic hyperplasia patients (see Example 5).

More particularly, in one embodiment of the present invention, as a result of performing metagenomic analysis on bacteria-derived extracellular vesicles at a genus level, the content of extracellular vesicles derived from bacteria belonging to the genus *Ruminococcus*, the genus *Akkermansia*, and the genus *Flexispira* was significantly different between prostate cancer patients and prostatic hyperplasia patients (see Example 5).

In another embodiment of the present invention, metagenomic analysis was performed on bacteria-derived extracellular vesicles in urine samples of normal individuals and prostatic hyperplasia patients, and bacteria-derived extracellular vesicles capable of acting as causes of the onset of prostate cancer were identified by analysis at phylum, class, order, family, and genus levels.

More particularly, in one embodiment of the present invention, as a result of performing metagenomic analysis on bacteria-derived extracellular vesicles at a phylum level, the content of extracellular vesicles derived from bacteria belonging to the phylum Euryarchaeota and the phylum Acidobacteria was significantly different between prostatic hyperplasia patients and normal individuals (see Example 6).

More particularly, in one embodiment of the present invention, as a result of performing metagenomic analysis on bacteria-derived extracellular vesicles at a class level, the content of extracellular vesicles derived from bacteria belonging to the class Methanobacteria, the class Acidobacteria, and the class Acidobacteriiawas was significantly different between prostatic hyperplasia patients and normal individuals (see Example 6).

More particularly, in one embodiment of the present invention, as a result of performing metagenomic analysis on bacteria-derived extracellular vesicles at an order level, the content of extracellular vesicles derived from bacteria belonging to the order Stramenopiles, the order RF39, the order Saprospirales, the order Pseudomonadales, the order Methanobacteriales, and the order Acidobacteriales was significantly different between prostatic hyperplasia patients and normal individuals (see Example 6).

More particularly, in one embodiment of the present invention, as a result of performing metagenomic analysis on bacteria-derived extracellular vesicles at a family level, the content of extracellular vesicles derived from bacteria belonging to the family Exiguobacteraceae, the family Flavobacteriaceae, the family Actinomycetaceae, the family Moraxellaceae, the family Ruminococcaceae, the family Rikenellaceae, the family Methanobacteriaceae, and the family Koribacteraceae was significantly different between prostatic hyperplasia patients and normal individuals (see Example 6).

More particularly, in one embodiment of the present invention, as a result of performing metagenomic analysis on bacteria-derived extracellular vesicles at a genus level, the content of extracellular vesicles derived from bacteria belonging to the genus *Rhizobium*, the genus *Proteus*, the genus *Acinetobacter*, the genus SMB53, the genus *Halomonas*, the genus *Ruminococcus*, the genus *Faecalibacterium*, the genus *Klebsiella*, the genus *Roseburia*, the genus *Leuconostoc*, the genus *Bilophila*, the genus *Chromohalobacter*, and the genus *Methanobrevibacter* was significantly different between prostatic hyperplasia patients and normal individuals (see Example 6).

From the above-described example results, it was confirmed that bacteria-derived extracellular vesicles exhibiting a significant change in content in prostate cancer patients compared to normal individuals and prostatic hyperplasia patients were identified by performing metagenomic analysis on bacteria-derived extracellular vesicles isolated from urine, and prostate cancer could be diagnosed by analyzing an increase or decrease in the content of bacteria-derived extracellular vesicles at each level through metagenomic analysis.

From the above-described example results, it was also confirmed that bacteria-derived extracellular vesicles exhibiting a significant change in content in prostatic hyperplasia patients compared to normal individuals were identified by performing metagenomic analysis on bacteria-derived extracellular vesicles isolated from urine, and a prostatic hyperplasia could be diagnosed by analyzing an increase or decrease in the content of bacteria-derived extracellular vesicles at each level through metagenomic analysis.

Hereinafter, the present invention will be described with reference to exemplary examples to aid in understanding of the present invention. However, these examples are provided only for illustrative purposes and are not intended to limit the scope of the present invention.

EXAMPLES

Example 1. Analysis of In Vivo Absorption, Distribution, and Excretion Patterns of Intestinal Bacteria and Bacteria-Derived Extracellular Vesicles To evaluate whether intestinal bacteria and bacteria-derived extracellular vesicles are systematically absorbed through the gastrointestinal tract, an experiment was conducted using the following method. More particularly, 50 μg of each of intestinal bacteria and the bacteria-derived extracellular vesicles (EVs), labeled with fluorescence, were orally administered to the gastrointestinal tracts of mice, and fluorescence was measured at 0 h, and after 5 min, 3 h, 6 h, and 12 h. As a result of observing the entire images of mice, as illustrated in FIG. 1A, the bacteria were not systematically absorbed when administered, while the bacteria-derived EVs were systematically absorbed at 5 min after administration, and, at 3 h after administration, fluorescence was strongly observed in the bladder, from which it was confirmed that the EVs were excreted via the urinary system, and were present in the bodies up to 12 h after administration.

Figure 1B:
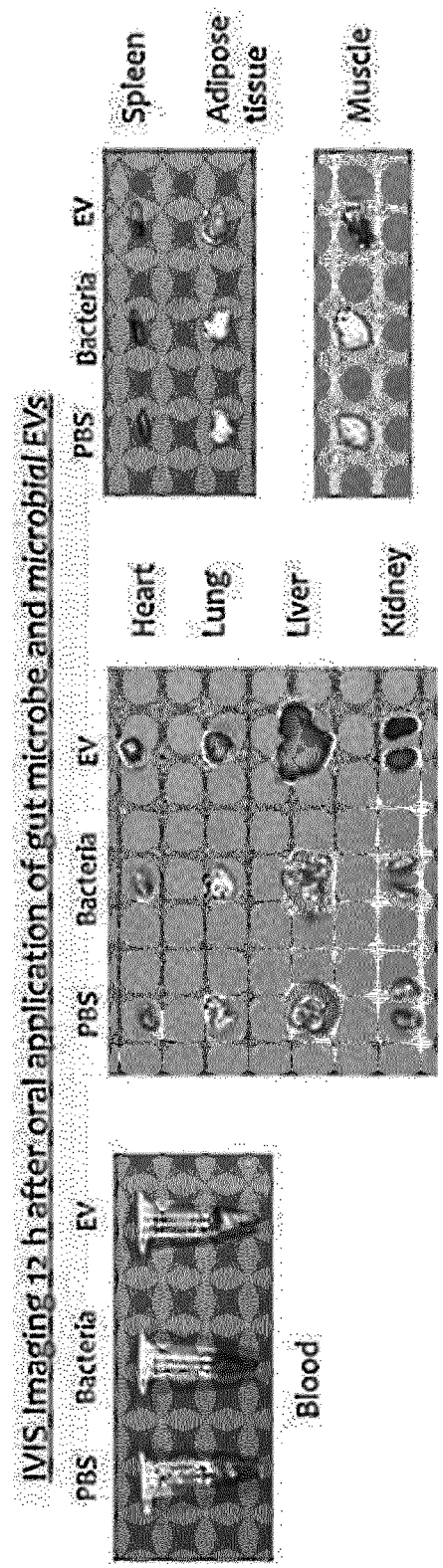

After intestinal bacteria and intestinal bacteria-derived extracellular vesicles were systematically absorbed, to evaluate a pattern of invasion of intestinal bacteria and the bacteria-derived EVs into various organs in the human body after being systematically absorbed, 50 μg of each of the bacteria and bacteria-derived EVs, labeled with fluorescence, were administered using the same method as that used above, and then, at 12 h after administration, blood, the heart, the lungs, the liver, the kidneys, the spleen, adipose tissue, and muscle were extracted from each mouse. As a result of observing fluorescence in the extracted tissues, as illustrated in FIG. 1B, it was confirmed that the intestinal bacteria were not absorbed into each organ, while the bacteria-derived EVs were distributed in the blood, heart, lungs, liver, kidneys, spleen, adipose tissue, and muscle.

Example 2. Vesicle Isolation and DNA Extraction from Urine

To isolate extracellular vesicles and extract DNA, from urine, first, urine was added to a 10 ml tube and centrifuged at 3,500×g and 4° C. for 10 min to precipitate a suspension, and only a supernatant was collected, which was then placed in a new 10 ml tube. The collected supernatant was filtered using a 0.22 μm filter to remove bacteria and impurities, and then placed in centripreigugal filters (50 kD) and centrifuged at 1500×g and 4° C. for 15 min to discard materials with a smaller size than 50 kD, and then concentrated to 10 ml. Once again, bacteria and impurities were removed therefrom using a 0.22 μm filter, and then the resulting concentrate was subjected to ultra-high speed centrifugation at 150,000×g and 4° C. for 3 hours by using a Type 90ti rotor to remove a supernatant, and the agglomerated pellet was dissolved with phosphate-buffered saline (PBS), thereby obtaining vesicles.

100 µl of the extracellular vesicles isolated from the urine according to the above-described method was boiled at 100° C. to allow the internal DNA to come out of the lipid and then cooled on ice. Next, the resulting vesicles were centrifuged at 10,000×g and 4° C. for 30 minutes to remove the remaining suspension, only the supernatant was collected, and then the amount of DNA extracted was quantified using a NanoDrop sprectrophotometer. In addition, to verify whether bacteria-derived DNA was present in the extracted DNA, PCR was performed using 16s rDNA primers shown in Table 1 below.

TABLE 1

| Primer | | Sequence | SEQ ID NO. |
|---|---|---|---|
| 16S rDNA | 16S_V3_F | 5'-TCGTCGGCAGCGTC AGATGTGTATAAGAG ACAGCCTACGGGNGG CWGCAG-3' | 1 |
| | 16S_V4_R | 5'-GTCTCGTGGGCTCG GAGATGTGTATAAGA GACAGGACTACHVGG GTATCTAATCC-3' | 2 |

Example 3. Metagenomic Analysis Using DNA Extracted from Vesicle in Urine

DNA was extracted using the same method as that used in Example 2, and then PCR was performed thereon using 16S rDNA primers shown in Table 1 to amplify DNA, followed by sequencing (Illumina MiSeq sequencer). The results were output as standard flowgram format (SFF) files, and the SFF files were converted into sequence files (.fasta) and nucleotide quality score files using GS FLX software (v2.9), and then credit rating for reads was identified, and portions with a window (20 bps) average base call accuracy of less than 99% (Phred score <20) were removed. After removing the low-quality portions, only reads having a length of 300 bps or more were used (Sickle version 1.33), and, for operational taxonomy unit (OTU) analysis, clustering was performed using UCLUST and USEARCH according to sequence similarity. In particular, clustering was performed based on sequence similarity values of 94% for genus, 90% for family, 85% for order, 80% for class, and 75% for phylum, and phylum, class, order, family, and genus levels of each OTU were classified, and bacteria with a sequence similarity of 97% or more were analyzed (QIIME) using 16S DNA sequence databases (108,453 sequences) of BLASTN and GreenGenes.

Example 4. Prostate Cancer Diagnostic Model Based on Metagenomic Analysis of Bacteria-Derived EVs Isolated from Urine of Normal Individuals and Prostate Cancer Patients EVs were isolated from urine samples of 53 prostate cancer patients and 159 normal individuals, the two groups matched in age and gender, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 2:
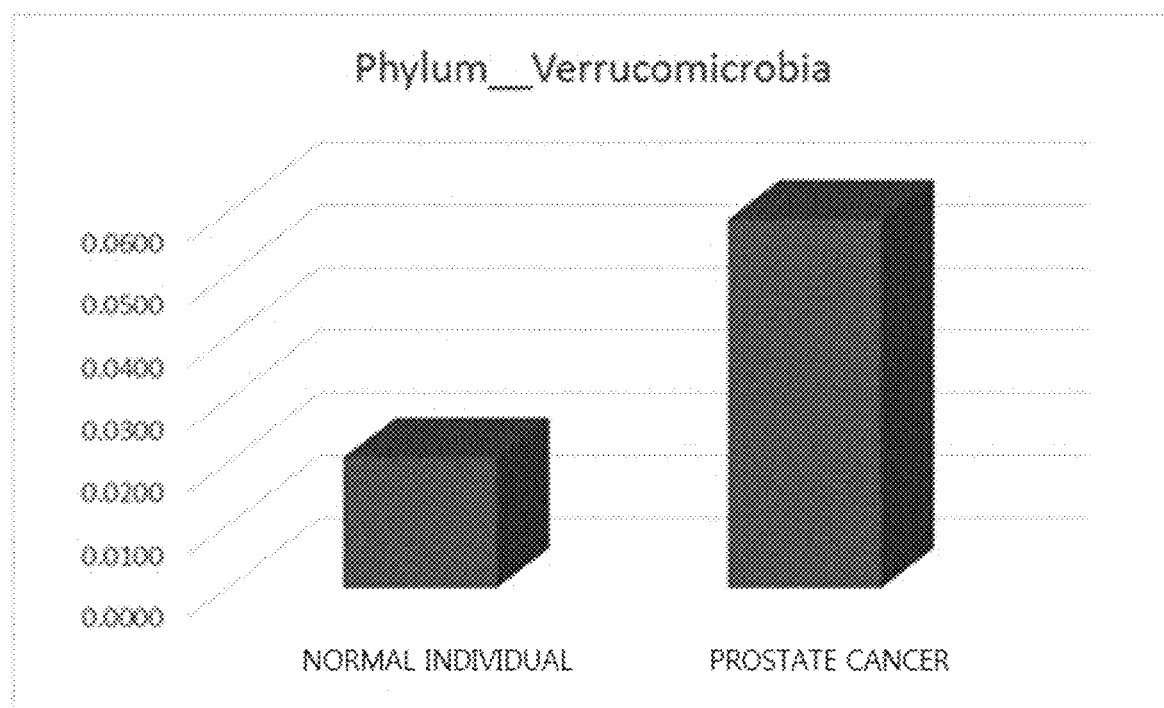
FIG. 2 illustrates distribution results of bacteria-derived EVs exhibiting significant diagnostic performance at a phylum level, after metagenomic analysis of bacteria-derived EVs isolated from prostate cancer patient-derived urine and normal individual-derived urine.
Figure 2:
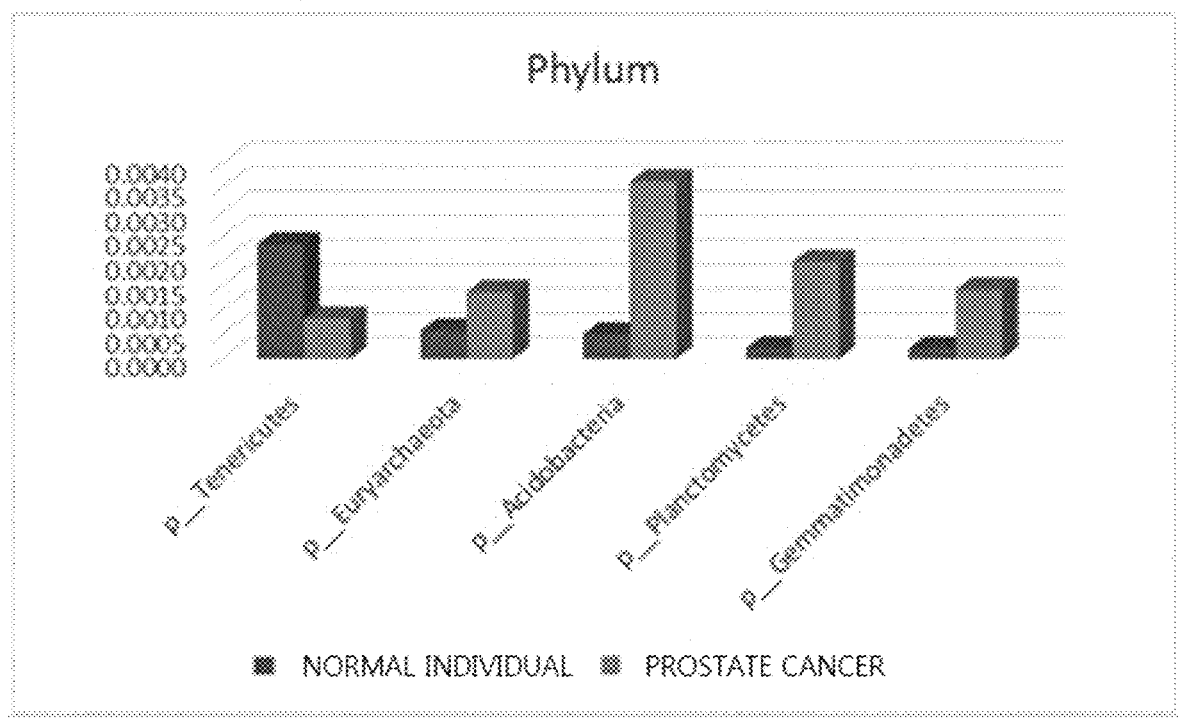

As a result of analyzing bacteria-derived extracellular vesicles in urine at a phylum level, a diagnostic model developed using, as a biomarker, one or more bacteria from the phylum Deferribacteres, the phylum Tenericutes, the phylum Actinobacteria, the phylum Acidobacteria, the phylum Armatimonadetes, the phylum Planctomycetes, and the phylum Fusobacteria exhibited significant diagnostic performance for prostate cancer (see Table 2 and FIG. 2).

TABLE 2

| Taxon | Normal Individual | | Prostate Cancer | | t-test | | | | |
|---|---|---|---|---|---|---|---|---|---|
| | Mean | SD | Mean | SD | p-value | Ratio | AUC | sensitivity | specificity |
| p__Tenericutes | 0.0023 | 0.0068 | 0.0008 | 0.0016 | 0.0096 | 0.35 | 0.88 | 0.93 | 0.58 |
| p__Euryarchaeota | 0.0006 | 0.0013 | 0.0014 | 0.0017 | 0.0032 | 2.38 | 0.87 | 0.91 | 0.55 |
| p__Verrucomicrobia | 0.0208 | 0.0283 | 0.0588 | 0.0564 | 0.0000 | 2.83 | 0.91 | 0.94 | 0.60 |
| p__Gemmatimonadetes | 0.0002 | 0.0007 | 0.0014 | 0.0021 | 0.0001 | 6.73 | 0.90 | 0.92 | 0.58 |
| p__Acidobacteria | 0.0005 | 0.0017 | 0.0036 | 0.0037 | 0.0000 | 7.19 | 0.91 | 0.92 | 0.58 |
| p__Planctomycetes | 0.0002 | 0.0010 | 0.0020 | 0.0046 | 0.0088 | 9.34 | 0.88 | 0.92 | 0.49 |

Figure 3:
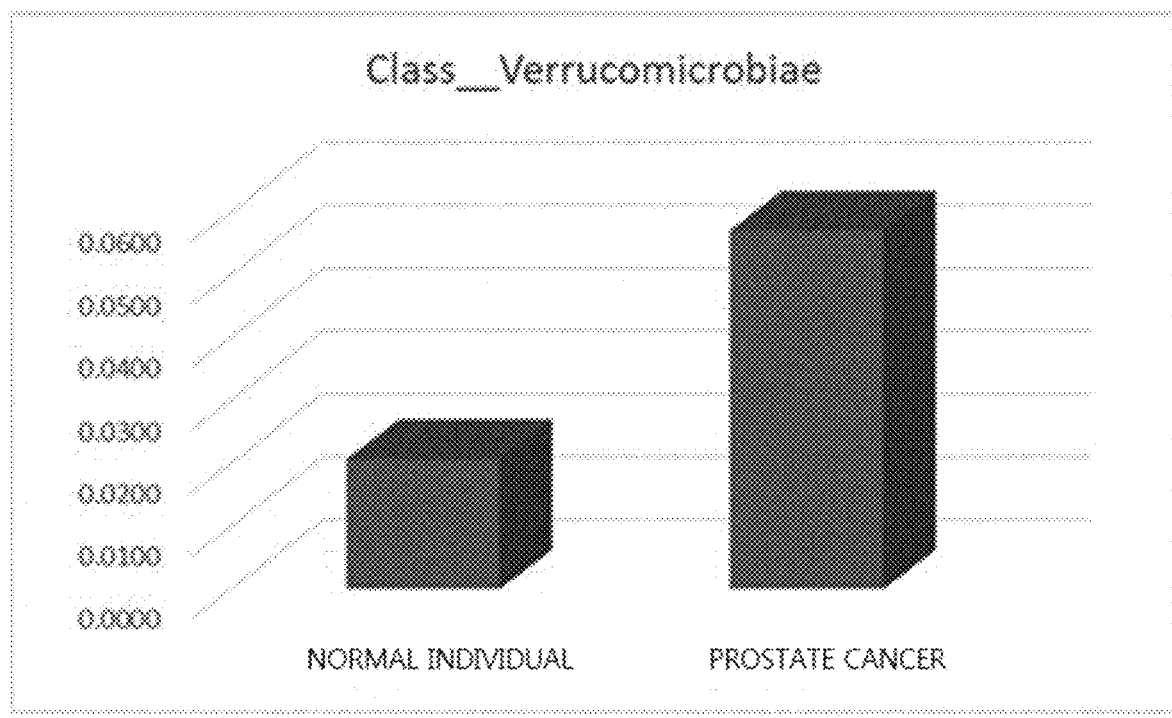
FIG. 3 illustrates distribution results of bacteria-derived EVs exhibiting significant diagnostic performance at a class level, after metagenomic analysis of bacteria-derived EVs isolated from prostate cancer patient-derived urine and normal individual-derived urine.
Figure 3:
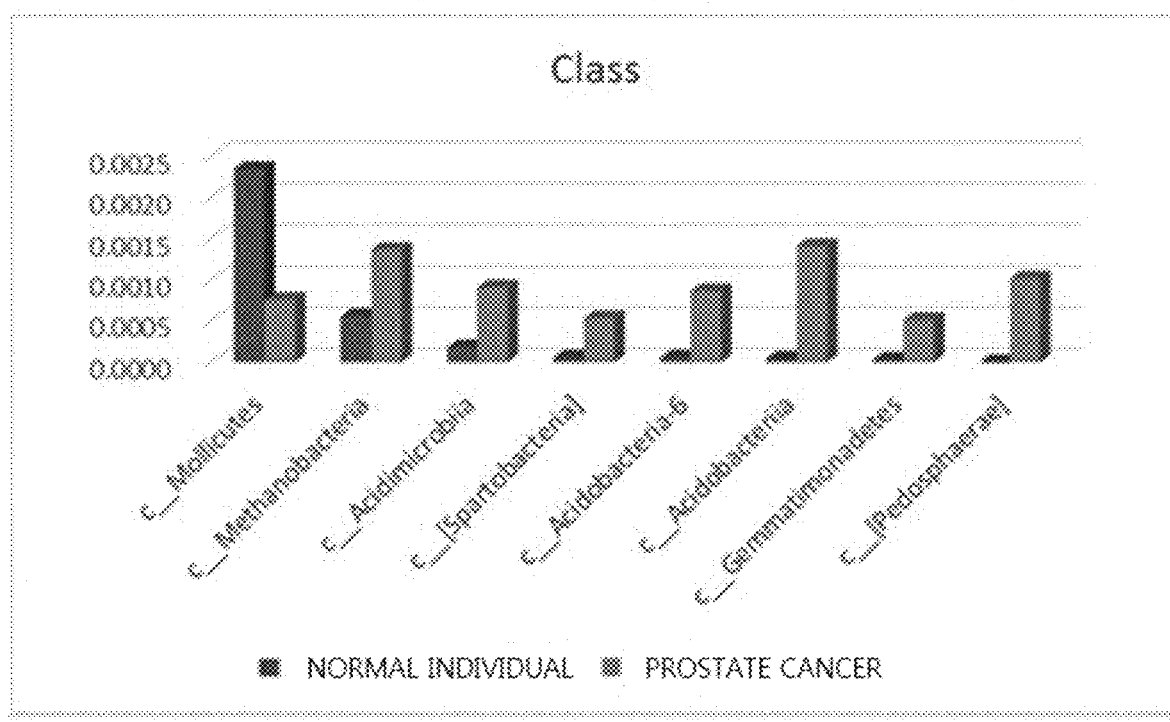

As a result of analyzing bacteria-derived extracellular vesicles in urine at a class level, a diagnostic model developed using, as a biomarker, one or more bacteria from the class Mollicutes, the class Methanobacteria, the class Verrucomicrobiae, the class Acidimicrobiia, the class Spartobacteria, the class Acidobacteria-6, the class Gemmatimonadetes, the class Acidobacteriia, and the class Pedosphaerae exhibited significant diagnostic performance for prostate cancer (see Table 3 and FIG. 3).

TABLE 3

| Taxon | Normal Individual | | Prostate Cancer | | t-test | | | | |
|---|---|---|---|---|---|---|---|---|---|
| | Mean | SD | Mean | SD | p-value | Ratio | AUC | sensitivity | specificity |
| c__Mollicutes | 0.0023 | 0.0068 | 0.0008 | 0.0015 | 0.0066 | 0.32 | 0.88 | 0.93 | 0.58 |
| c__Methanobacteria | 0.0006 | 0.0012 | 0.0014 | 0.0017 | 0.0028 | 2.45 | 0.87 | 0.91 | 0.55 |
| c__Verrucomicrobiae | 0.0206 | 0.0281 | 0.0570 | 0.0551 | 0.0000 | 2.76 | 0.91 | 0.94 | 0.60 |

TABLE 3-continued

| Taxon | Normal Individual Mean | SD | Prostate Cancer Mean | SD | t-test p-value | Ratio | AUC | sensitivity | specificity |
|---|---|---|---|---|---|---|---|---|---|
| c__Acidimicrobiia | 0.0002 | 0.0010 | 0.0009 | 0.0017 | 0.0043 | 5.00 | 0.85 | 0.91 | 0.43 |
| c__[Spartobacteria] | 0.0001 | 0.0004 | 0.0005 | 0.0008 | 0.0002 | 9.75 | 0.89 | 0.92 | 0.57 |
| c__Acidobacteria-6 | 0.0001 | 0.0003 | 0.0009 | 0.0017 | 0.0013 | 16.28 | 0.89 | 0.92 | 0.53 |
| c__Gemmatimonadetes | 0.0000 | 0.0002 | 0.0005 | 0.0011 | 0.0023 | 16.65 | 0.87 | 0.93 | 0.51 |
| c__Acidobacteriia | 0.0000 | 0.0002 | 0.0014 | 0.0018 | 0.0000 | 33.12 | 0.92 | 0.93 | 0.60 |
| c__[Pedosphaerae] | 0.0000 | 0.0000 | 0.0010 | 0.0017 | 0.0001 | 2689.17 | 0.93 | 0.95 | 0.68 |

Figure 4:
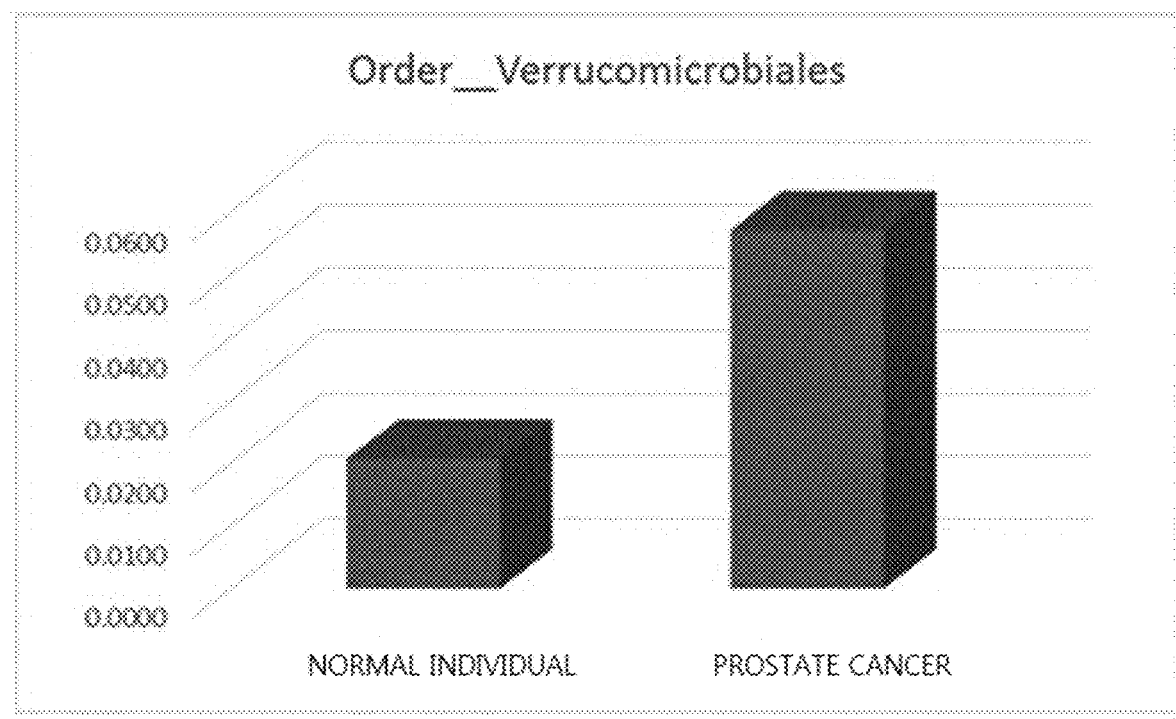
FIG. 4 illustrates distribution results of bacteria-derived EVs exhibiting significant diagnostic performance at an order level, after metagenomic analysis of bacteria-derived EVs isolated from prostate cancer patient-derived urine and normal individual-derived urine.
Figure 4:
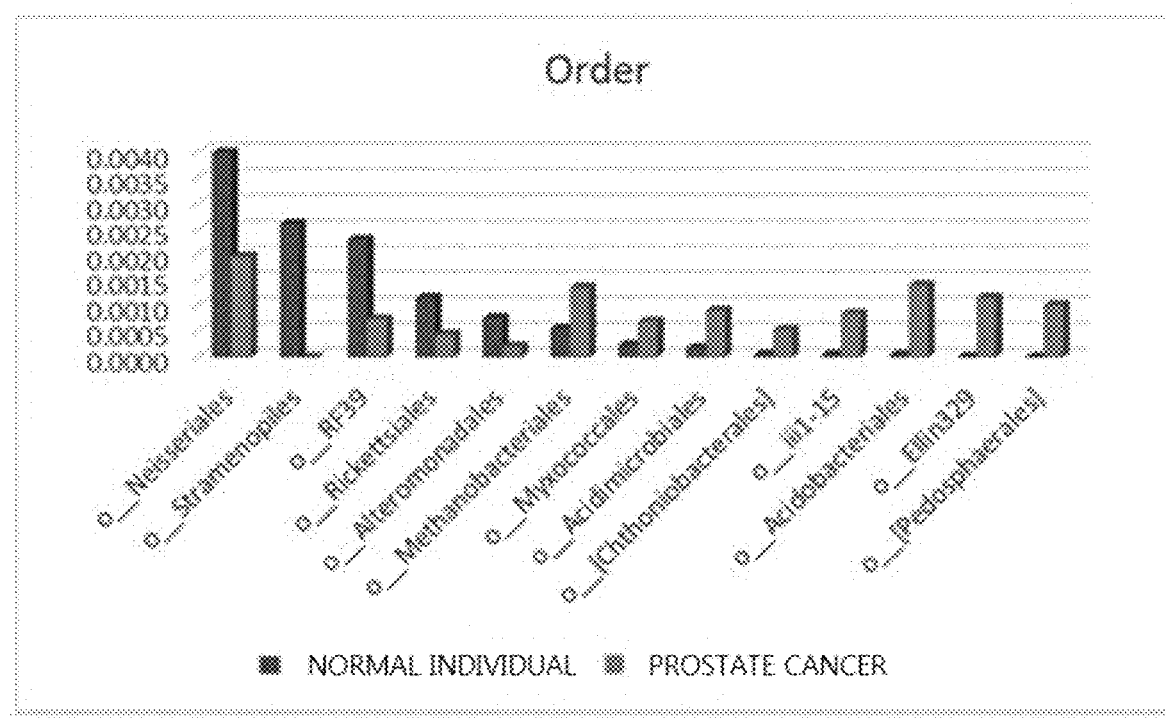

As a result of analyzing bacteria-derived extracellular vesicles in urine at an order level, a diagnostic model developed using, as a biomarker, one or more bacteria from the order Stramenopiles, the order Alteromonadales, the order RF39, the order Rickettsiales, the order Neisseriales, the order Methanobacteriales, the order Verrucomicrobiales, the order Myxococcales, the order Acidimicrobiales, the order Chthoniobacterales, the order iii1-15, the order Acidobacteriales, the order Ellin329, and the order Pedosphaerales exhibited significant diagnostic performance for prostate cancer (see Table 4 and FIG. 4).

TABLE 4

| Taxon | Normal Individual Mean | SD | Prostate Cancer Mean | SD | t-test p-value | Ratio | AUC | sensitivity | specificity |
|---|---|---|---|---|---|---|---|---|---|
| o__Stramenopiles | 0.0026 | 0.0059 | 0.0000 | 0.0000 | 0.0000 | 0.00 | 0.87 | 0.86 | 0.49 |
| o__Alteromonadales | 0.0008 | 0.0020 | 0.0002 | 0.0008 | 0.0015 | 0.28 | 0.85 | 0.90 | 0.40 |
| o__RF39 | 0.0023 | 0.0068 | 0.0007 | 0.0015 | 0.0077 | 0.32 | 0.88 | 0.93 | 0.58 |
| o__Rickettsiales | 0.0012 | 0.0027 | 0.0004 | 0.0008 | 0.0042 | 0.38 | 0.84 | 0.91 | 0.40 |
| o__Neisseriales | 0.0040 | 0.0066 | 0.0020 | 0.0025 | 0.0011 | 0.49 | 0.86 | 0.88 | 0.43 |
| o__Methanobacteriales | 0.0006 | 0.0012 | 0.0014 | 0.0017 | 0.0028 | 2.45 | 0.87 | 0.91 | 0.55 |
| o__Verrucomicrobiales | 0.0206 | 0.0281 | 0.0570 | 0.0551 | 0.0000 | 2.76 | 0.91 | 0.94 | 0.60 |
| o__Myxococcales | 0.0002 | 0.0008 | 0.0007 | 0.0010 | 0.0044 | 2.87 | 0.85 | 0.89 | 0.49 |
| o__Acidimicrobiales | 0.0002 | 0.0010 | 0.0009 | 0.0017 | 0.0043 | 5.00 | 0.85 | 0.91 | 0.43 |
| o__[Chthoniobacterales] | 0.0001 | 0.0004 | 0.0005 | 0.0008 | 0.0002 | 9.75 | 0.89 | 0.92 | 0.57 |
| o__iii1-15 | 0.0000 | 0.0003 | 0.0008 | 0.0017 | 0.0014 | 18.60 | 0.89 | 0.92 | 0.53 |
| o__Acidobacteriales | 0.0000 | 0.0002 | 0.0014 | 0.0018 | 0.0000 | 33.12 | 0.92 | 0.93 | 0.60 |
| o__Ellin329 | 0.0000 | 0.0000 | 0.0012 | 0.0018 | 0.0000 | 365.18 | 0.91 | 0.96 | 0.58 |
| o__[Pedosphaerales] | 0.0000 | 0.0000 | 0.0010 | 0.0017 | 0.0001 | 2689.17 | 0.93 | 0.95 | 0.68 |

Figure 5:
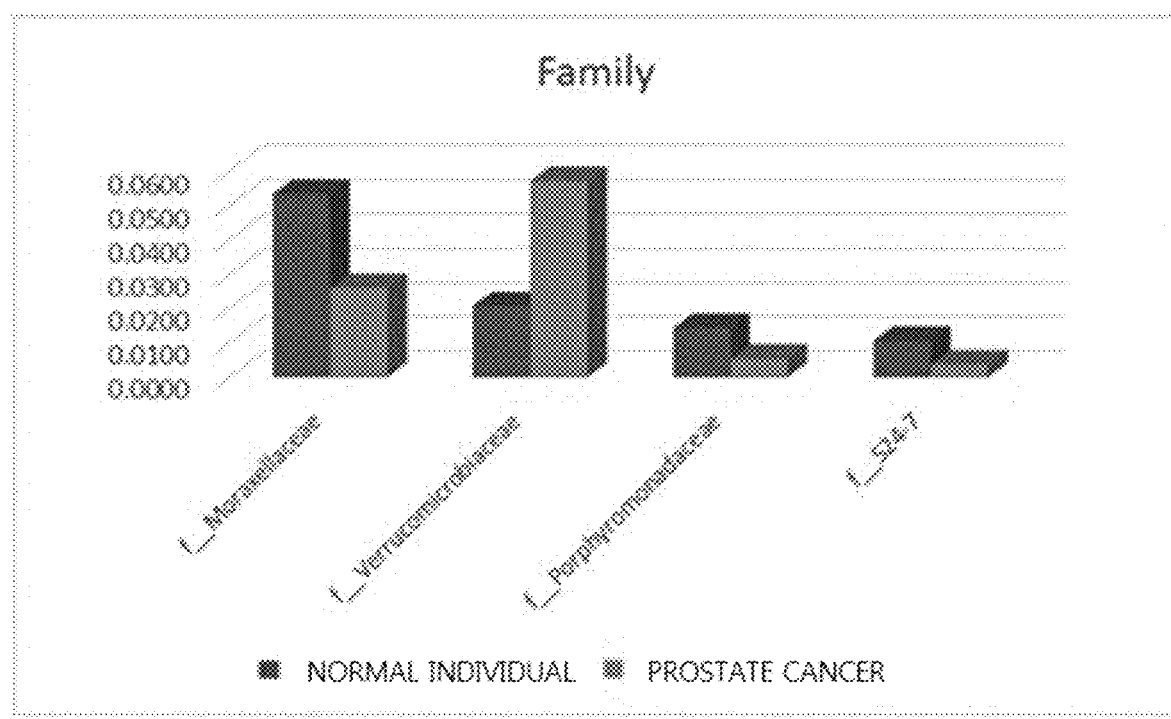
FIG. 5 illustrates distribution results of bacteria-derived EVs exhibiting significant diagnostic performance at a family level, after metagenomic analysis of bacteria-derived EVs isolated from prostate cancer patient-derived urine and normal individual-derived urine.
Figure 5:
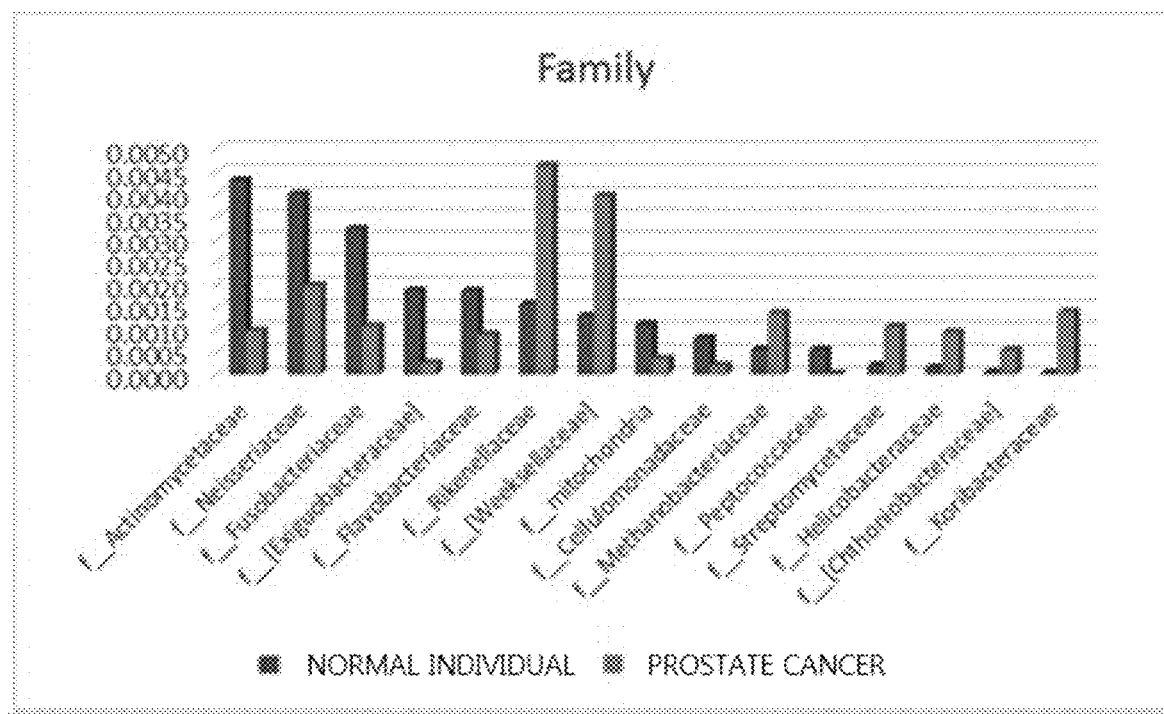

As a result of analyzing bacteria-derived extracellular vesicles in urine at a family level, a diagnostic model developed using, as a biomarker, one or more bacteria from the family Peptococcaceae, the family Exiguobacteraceae, the family Actinomycetaceae, the family Cellulomonadaceae, the family Mitochondria, the family Fusobacteriaceae, the family S24-7, the family Porphyromonadaceae, the family Flavobacteriaceae, the family Moraxellaceae, the family Neisseriaceae, the family Methanobacteriaceae, the family Verrucomicrobiaceae, the family Rikenellaceae, the family Weeksellaceae, the family Streptomycetaceae, the family Helicobacteraceae, the family Chthoniobacteraceae, and the family Koribacteraceae exhibited significant diagnostic performance for prostate cancer (see Table 5 and FIG. 5).

TABLE 5

| Taxon | Normal Individual Mean | SD | Prostate Cancer Mean | SD | t-test p-value | Ratio | AUC | Accuracy | sensitivity | specificity |
|---|---|---|---|---|---|---|---|---|---|---|
| f__Peptococcaceae | 0.0005 | 0.0018 | 0.0000 | 0.0000 | 0.0002 | 0.03 | 0.88 | 0.80 | 0.91 | 0.49 |
| f__[Exiguobacteraceae] | 0.0019 | 0.0065 | 0.0003 | 0.0008 | 0.0027 | 0.14 | 0.84 | 0.77 | 0.90 | 0.38 |
| f__Actinomycetaceae | 0.0043 | 0.0102 | 0.0010 | 0.0015 | 0.0001 | 0.23 | 0.89 | 0.80 | 0.87 | 0.58 |
| f__Cellulomonadaceae | 0.0008 | 0.0021 | 0.0002 | 0.0005 | 0.0011 | 0.25 | 0.86 | 0.77 | 0.89 | 0.40 |
| f__mitochondria | 0.0011 | 0.0027 | 0.0003 | 0.0007 | 0.0016 | 0.31 | 0.84 | 0.87 | 0.92 | 0.38 |
| f__Fusobacteriaceae | 0.0032 | 0.0095 | 0.0011 | 0.0018 | 0.0070 | 0.33 | 0.85 | 0.77 | 0.91 | 0.38 |
| f__S24-7 | 0.0104 | 0.0319 | 0.0036 | 0.0042 | 0.0098 | 0.35 | 0.83 | 0.87 | 0.92 | 0.38 |
| f__Porphyromonadaceae | 0.0142 | 0.0158 | 0.0053 | 0.0045 | 0.0000 | 0.37 | 0.85 | 0.77 | 0.88 | 0.45 |
| f__Flavobacteriaceae | 0.0019 | 0.0030 | 0.0009 | 0.0016 | 0.0035 | 0.48 | 0.85 | 0.76 | 0.89 | 0.38 |
| f__Moraxellaceae | 0.0532 | 0.0884 | 0.0260 | 0.0275 | 0.0008 | 0.49 | 0.89 | 0.81 | 0.91 | 0.51 |
| f__Neisseriaceae | 0.0040 | 0.0066 | 0.0020 | 0.0025 | 0.0011 | 0.49 | 0.86 | 0.77 | 0.88 | 0.43 |
| f__Methanobacteriaceae | 0.0006 | 0.0012 | 0.0014 | 0.0017 | 0.0028 | 2.45 | 0.87 | 0.82 | 0.91 | 0.55 |
| f__Verrucomicrobiaceae | 0.0206 | 0.0281 | 0.0570 | 0.0551 | 0.0000 | 2.76 | 0.91 | 0.85 | 0.94 | 0.60 |
| f__Rikenellacea | 0.0016 | 0.0026 | 0.0046 | 0.0043 | 0.0000 | 2.98 | 0.89 | 0.81 | 0.90 | 0.53 |
| f__[Weeksellaceae] | 0.0013 | 0.0022 | 0.0040 | 0.0049 | 0.0003 | 3.06 | 0.88 | 0.83 | 0.92 | 0.53 |
| f__Streptomycetaceae | 0.0002 | 0.0008 | 0.0011 | 0.0022 | 0.0075 | 5.21 | 0.85 | 0.77 | 0.89 | 0.42 |
| f__Helicobacteraceae | 0.0002 | 0.0011 | 0.0009 | 0.0020 | 0.0092 | 6.08 | 0.86 | 0.81 | 0.92 | 0.47 |

TABLE 5-continued

|  | Normal Individual | | Prostate Cancer | | t-test | | | | | |
|---|---|---|---|---|---|---|---|---|---|---|
| Taxon | Mean | SD | Mean | SD | p-value | Ratio | AUC | Accuracy | sensitivity | specificity |
| f__[Chthoniobacteraceae] | 0.0001 | 0.0004 | 0.0005 | 0.0008 | 0.0002 | 9.75 | 0.89 | 0.83 | 0.92 | 0.57 |
| f__Koribacteraceae | 0.0000 | 0.0002 | 0.0014 | 0.0018 | 0.0000 | 43.84 | 0.92 | 0.85 | 0.94 | 0.60 |

Figure 6:
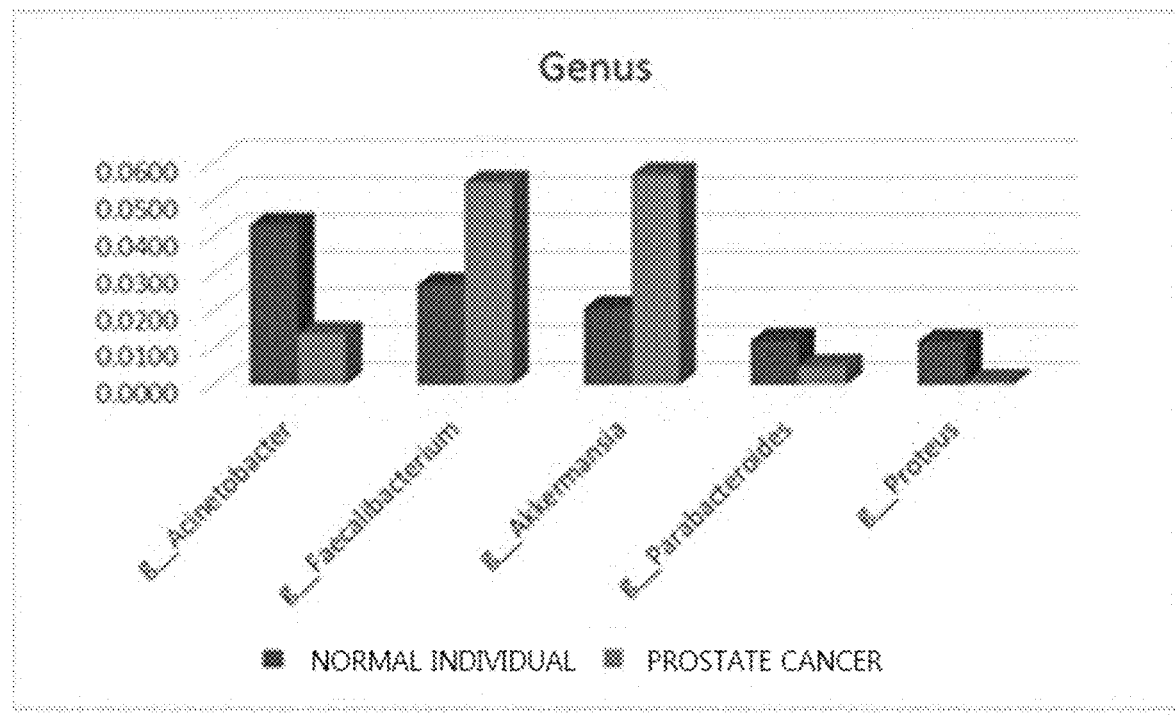
FIG. 6 illustrates distribution results of bacteria-derived EVs exhibiting significant diagnostic performance at a genus level, after metagenomic analysis of bacteria-derived EVs isolated from prostate cancer patient-derived urine and normal individual-derived urine.
Figure 6:
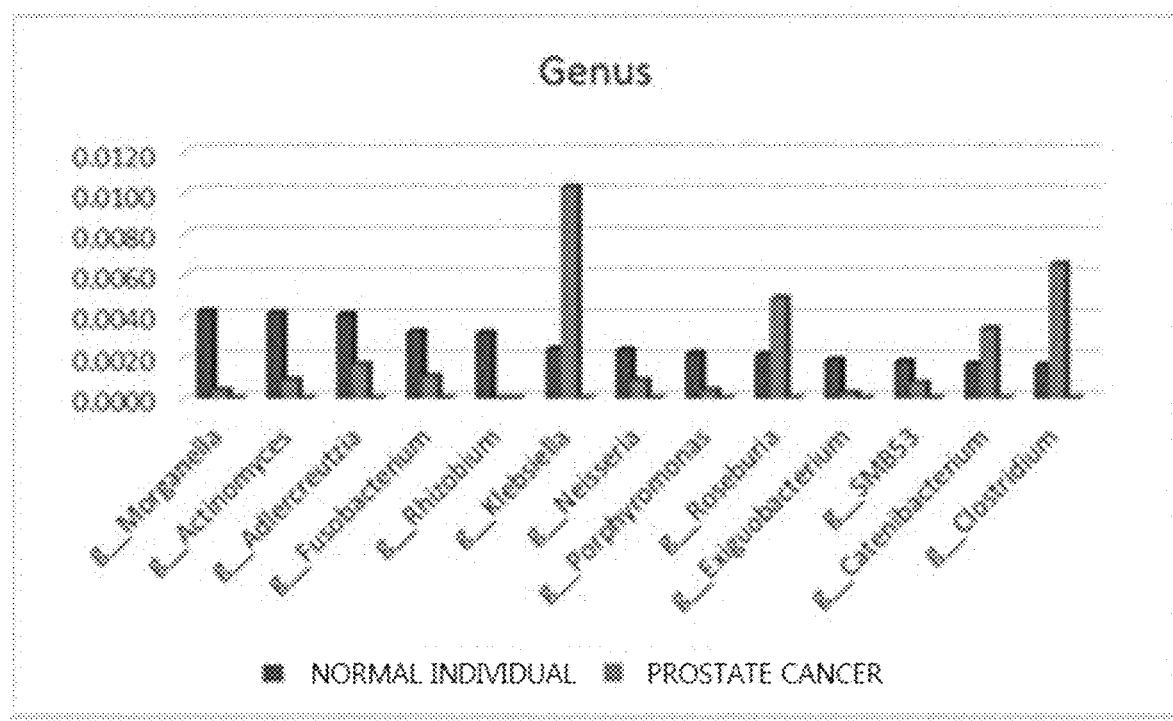

As a result of analyzing bacteria-derived extracellular vesicles in urine at a genus level, a diagnostic model developed using, as a biomarker, one or more bacteria from the genus *Rhizobium*, the genus *Tetragenococcus*, the genus *Proteus*, the genus *Morganella*, the genus *Exiguobacterium*, the genus *Oribacterium*, the genus *Porphyromonas*, the genus *Actinomyces*, the genus *Cellulomonas*, the genus *Jeotgalicoccus*, the genus *Acinetobacter*, the genus *Fusobacterium*, the genus *Enterobacter*, the genus *Neisseria*, the genus *Adlercreutzia*, the genus SMB53, the genus *Parabacteroides*, the genus *Faecalibacterium*, the genus *Catenibacterium*, the genus *Roseburia*, the genus *Akkermansia*, the genus *Methanobrevibacter*, the genus *Clostridium*, the genus *Klebsiella*, the genus *Chryseobacterium*, the genus *Halomonas*, the genus *Aggregatibacter*, the genus *Rhodoplanes*, the genus *Thermoanaerobacterium*, the genus *Candidatus Koribacter*, and the genus *Flexispira* exhibited significant diagnostic performance for prostate cancer (see Table 6 and FIG. 6).

Example 5. Prostate Cancer Diagnostic Model Based on Metagenomic Analysis of Bacteria-Derived EVs Isolated from Urine of Prostatic Hyperplasia Patients and Prostate Cancer Patients EVs were isolated from urine samples of 53 prostate cancer patients and 55 prostatic hyperplasia patients, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 7:
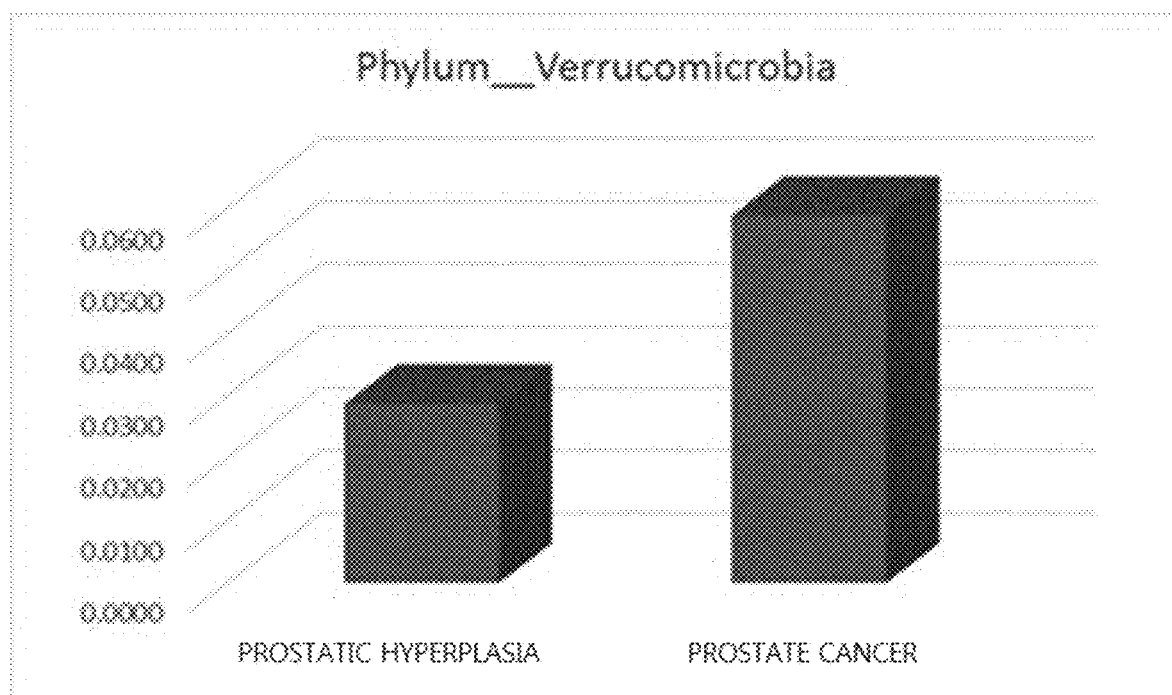
FIG. 7 illustrates distribution results of bacteria-derived EVs exhibiting significant diagnostic performance at a phylum level, after metagenomic analysis of bacteria-derived EVs isolated from prostate cancer patient-derived urine and prostatic hyperplasia patient-derived urine.

As a result of analyzing bacteria-derived extracellular vesicles in urine at a phylum level, a diagnostic model developed using, as a biomarker, bacteria belonging to the phylum Verrucomicrobia exhibited significant diagnostic performance for prostate cancer (see Table 7 and FIG. 7).

TABLE 6

|  | Normal Individual | | Prostate Cancer | | t-test | | | | |
|---|---|---|---|---|---|---|---|---|---|
| Taxon | Mean | SD | Mean | SD | p-value | Ratio | AUC | sensitivity | specificity |
| g__Rhizobium | 0.0032 | 0.0050 | 0.0000 | 0.0000 | 0.0000 | 0.00 | 0.98 | 0.98 | 0.94 |
| g__Tetragenococcus | 0.0007 | 0.0020 | 0.0000 | 0.0000 | 0.0000 | 0.01 | 0.86 | 0.90 | 0.42 |
| g__Proteus | 0.0115 | 0.0202 | 0.0009 | 0.0013 | 0.0000 | 0.07 | 0.92 | 0.90 | 0.68 |
| g__Morganella | 0.0042 | 0.0169 | 0.0004 | 0.0010 | 0.0050 | 0.09 | 0.85 | 0.91 | 0.38 |
| g__Exiguobacterium | 0.0019 | 0.0065 | 0.0002 | 0.0008 | 0.0026 | 0.13 | 0.84 | 0.90 | 0.38 |
| g__Oribacterium | 0.0005 | 0.0014 | 0.0001 | 0.0004 | 0.0016 | 0.13 | 0.85 | 0.91 | 0.42 |
| g__Porphyromonas | 0.0022 | 0.0062 | 0.0004 | 0.0010 | 0.0005 | 0.18 | 0.86 | 0.89 | 0.43 |
| g__Actinomyces | 0.0041 | 0.0099 | 0.0009 | 0.0015 | 0.0001 | 0.21 | 0.89 | 0.87 | 0.58 |
| g__Cellulomonas | 0.0006 | 0.0017 | 0.0002 | 0.0005 | 0.0045 | 0.27 | 0.86 | 0.89 | 0.38 |
| g__Jeotgalicoccus | 0.0009 | 0.0020 | 0.0003 | 0.0007 | 0.0007 | 0.30 | 0.85 | 0.91 | 0.36 |
| g__Acinetobacter | 0.0431 | 0.0871 | 0.0136 | 0.0185 | 0.0001 | 0.32 | 0.89 | 0.90 | 0.64 |
| g__Fusobacterium | 0.0032 | 0.0095 | 0.0011 | 0.0018 | 0.0073 | 0.33 | 0.85 | 0.91 | 0.38 |
| g__Enterobacter | 0.0005 | 0.0013 | 0.0002 | 0.0004 | 0.0050 | 0.37 | 0.83 | 0.92 | 0.38 |
| g__Neisseria | 0.0023 | 0.0044 | 0.0009 | 0.0013 | 0.0003 | 0.37 | 0.86 | 0.88 | 0.43 |
| g__Adlercreutzia | 0.0041 | 0.0076 | 0.0016 | 0.0021 | 0.0004 | 0.40 | 0.84 | 0.92 | 0.38 |
| g_SMB53 | 0.0018 | 0.0029 | 0.0007 | 0.0007 | 0.0000 | 0.41 | 0.90 | 0.94 | 0.55 |
| g__Parabacteroides | 0.0118 | 0.0148 | 0.0049 | 0.0044 | 0.0000 | 0.41 | 0.84 | 0.90 | 0.42 |
| g__Faecalibacterium | 0.0269 | 0.0355 | 0.0544 | 0.0408 | 0.0000 | 2.02 | 0.90 | 0.91 | 0.58 |
| g__Catenibacterium | 0.0017 | 0.0032 | 0.0034 | 0.0038 | 0.0013 | 2.05 | 0.84 | 0.89 | 0.43 |
| g__Roseburia | 0.0021 | 0.0040 | 0.0049 | 0.0059 | 0.0027 | 2.30 | 0.87 | 0.91 | 0.57 |
| g__Akkermansia | 0.0205 | 0.0280 | 0.0566 | 0.0550 | 0.0000 | 2.76 | 0.91 | 0.94 | 0.62 |
| g__Methanobrevibacter | 0.0004 | 0.0009 | 0.0013 | 0.0017 | 0.0003 | 3.59 | 0.88 | 0.91 | 0.55 |
| g__Clostridium | 0.0016 | 0.0039 | 0.0065 | 0.0064 | 0.0000 | 4.08 | 0.90 | 0.91 | 0.60 |
| g__Klebsiella | 0.0024 | 0.0046 | 0.0103 | 0.0123 | 0.0000 | 4.30 | 0.94 | 0.91 | 0.72 |
| g__Chryseobacterium | 0.0006 | 0.0016 | 0.0026 | 0.0031 | 0.0000 | 4.33 | 0.88 | 0.91 | 0.53 |
| g__Halomonas | 0.0003 | 0.0007 | 0.0015 | 0.0031 | 0.0097 | 4.41 | 0.87 | 0.92 | 0.51 |
| g__Aggregatibacter | 0.0001 | 0.0004 | 0.0011 | 0.0025 | 0.0067 | 8.42 | 0.85 | 0.92 | 0.47 |
| g__Rhodoplanes | 0.0000 | 0.0002 | 0.0006 | 0.0014 | 0.0075 | 18.08 | 0.87 | 0.92 | 0.49 |
| g__Thermoanaerobacterium | 0.0002 | 0.0011 | 0.0033 | 0.0050 | 0.0000 | 20.92 | 0.91 | 0.95 | 0.57 |
| g__Candidates Koribacter | 0.0000 | 0.0001 | 0.0007 | 0.0012 | 0.0002 | 45.87 | 0.90 | 0.94 | 0.55 |
| g__Flexispira | 0.0000 | 0.0000 | 0.0008 | 0.0019 | 0.0000 |  | 0.91 | 0.96 | 0.60 |

TABLE 7

| Taxon | Prostate Hyperplasia | | Prostate Cancer | | t-test | | | | |
|---|---|---|---|---|---|---|---|---|---|
| | Mean | SD | Mean | SD | p-value | Ratio | AUC | sensitivity | specificity |
| p__Verrucomicrobia | 0.0286 | 0.0414 | 0.0588 | 0.0573 | 0.0023 | 2.06 | 0.85 | 0.84 | 0.83 |

Figure 8:
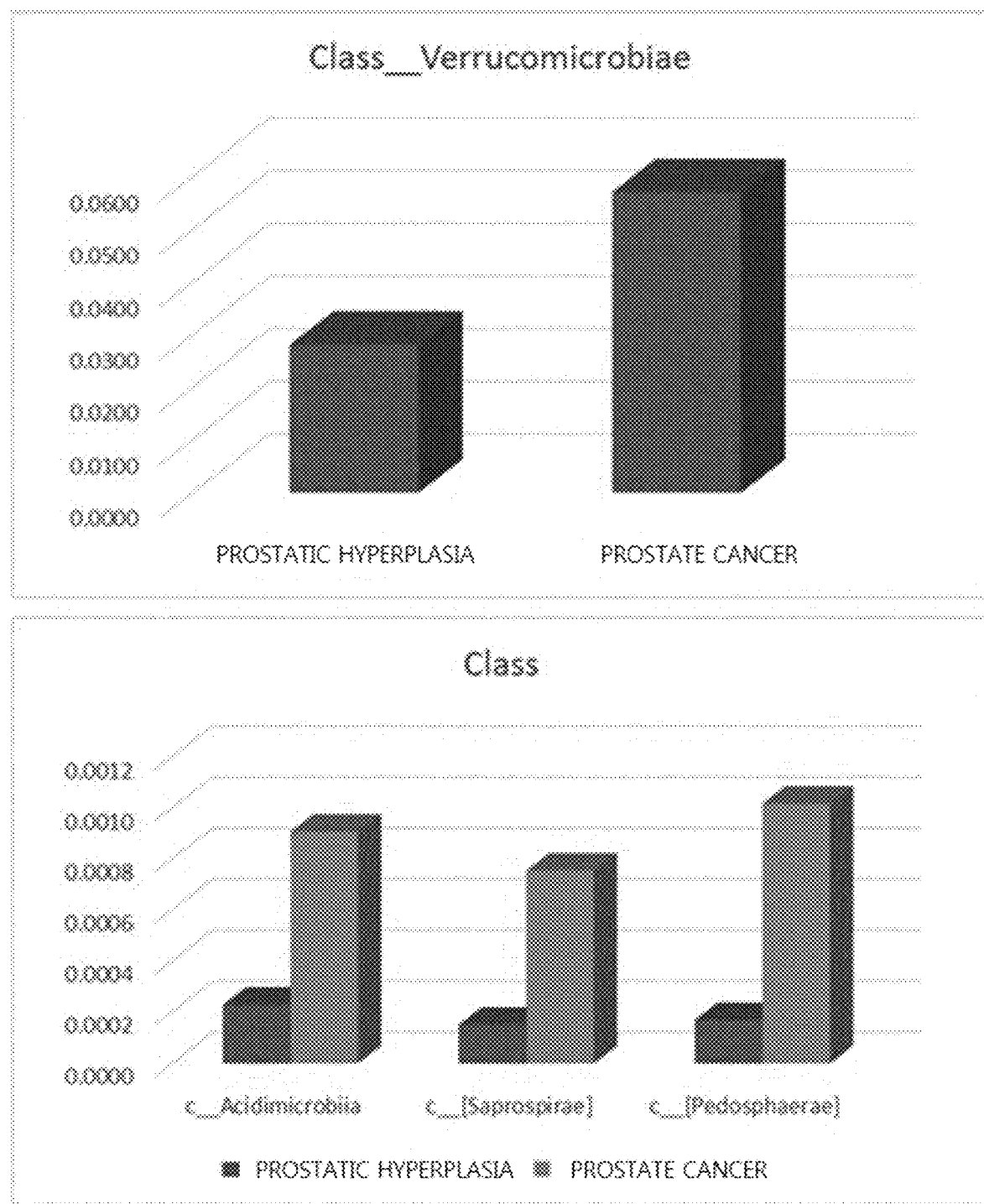
FIG. 8 illustrates distribution results of bacteria-derived EVs exhibiting significant diagnostic performance at a class level, after metagenomic analysis of bacteria-derived EVs isolated from prostate cancer patient-derived urine and prostatic hyperplasia patient-derived urine.

As a result of analyzing bacteria-derived extracellular vesicles in urine at a class level, a diagnostic model developed using, as a biomarker, one or more bacteria from the class Verrucomicrobiae, the class Acidimicrobiia, the class Saprospirae, and the class Pedosphaerae exhibited significant diagnostic performance for prostate cancer (see Table 8 and FIG. 8).

TABLE 8

| Taxon | Prostate Hyperplasia | | Prostate Cancer | | t-test | | | | |
|---|---|---|---|---|---|---|---|---|---|
| | Mean | SD | Mean | SD | p-value | Ratio | AUC | sensitivity | specificity |
| c__Verrucomicrobiae | 0.0281 | 0.0405 | 0.0570 | 0.0561 | 0.0028 | 2.03 | 0.85 | 0.82 | 0.83 |
| c__Acidimicrobiia | 0.0002 | 0.0007 | 0.0009 | 0.0017 | 0.0086 | 3.97 | 0.84 | 0.75 | 0.77 |
| c__[Saprospirae] | 0.0002 | 0.0005 | 0.0008 | 0.0011 | 0.0006 | 5.00 | 0.84 | 0.76 | 0.79 |
| c__[Pedosphaerae] | 0.0002 | 0.0005 | 0.0010 | 0.0017 | 0.0009 | 6.03 | 0.85 | 0.78 | 0.81 |

Figure 9:
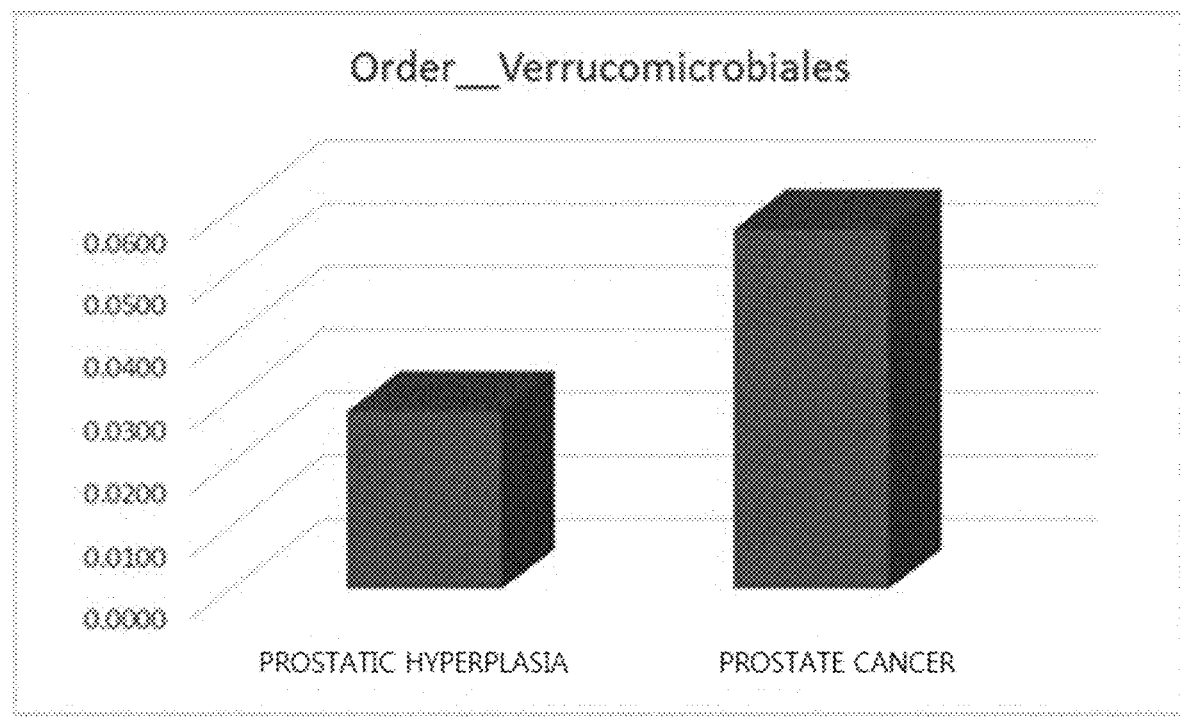
FIG. 9 illustrates distribution results of bacteria-derived EVs exhibiting significant diagnostic performance at an order level, after metagenomic analysis of bacteria-derived EVs isolated from prostate cancer patient-derived urine and prostatic hyperplasia patient-derived urine.
Figure 9:
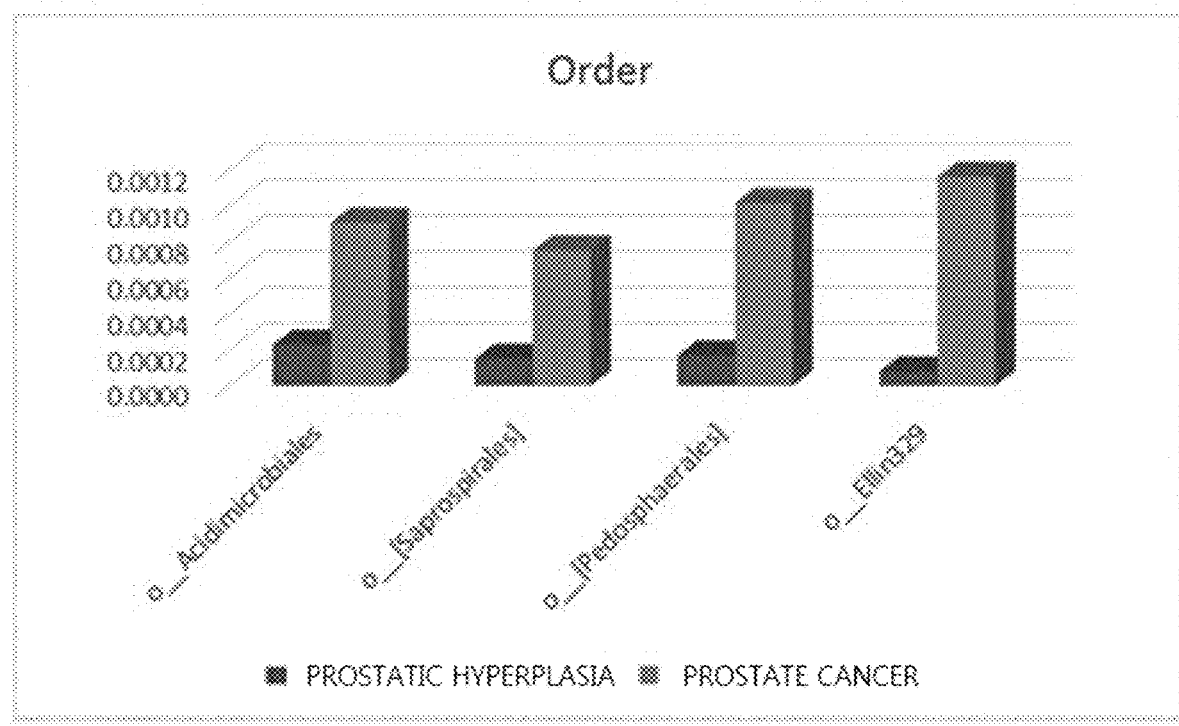

As a result of analyzing bacteria-derived extracellular vesicles in urine at an order level, a diagnostic model developed using, as a biomarker, one or more bacteria from the order Verrucomicrobiales, the order Acidimicrobiales, the order Saprospirales, the order Pedosphaerales, and the order Ellin329 exhibited significant diagnostic performance for prostate cancer (see Table 9 and FIG. 9).

TABLE 9

| Taxon | Prostate Hyperplasia | | Prostate Cancer | | t-test | | | | |
|---|---|---|---|---|---|---|---|---|---|
| | Mean | SD | Mean | SD | p-value | Ratio | AUC | sensitivity | specificity |
| o__Verrucomicrobiales | 0.0281 | 0.0405 | 0.0570 | 0.0561 | 0.0028 | 2.03 | 0.85 | 0.82 | 0.83 |
| o__Acidimicrobiales | 0.0002 | 0.0007 | 0.0009 | 0.0017 | 0.0086 | 3.94 | 0.84 | 0.75 | 0.77 |
| o__[Saprospirales] | 0.0002 | 0.0005 | 0.0008 | 0.0011 | 0.0006 | 5.00 | 0.84 | 0.76 | 0.79 |
| o__[Pedosphaerales] | 0.0002 | 0.0005 | 0.0010 | 0.0017 | 0.0009 | 6.03 | 0.85 | 0.78 | 0.81 |
| o__Ellin329 | 0.0001 | 0.0004 | 0.0012 | 0.0018 | 0.0001 | 14.59 | 0.87 | 0.85 | 0.77 |

Figure 10:
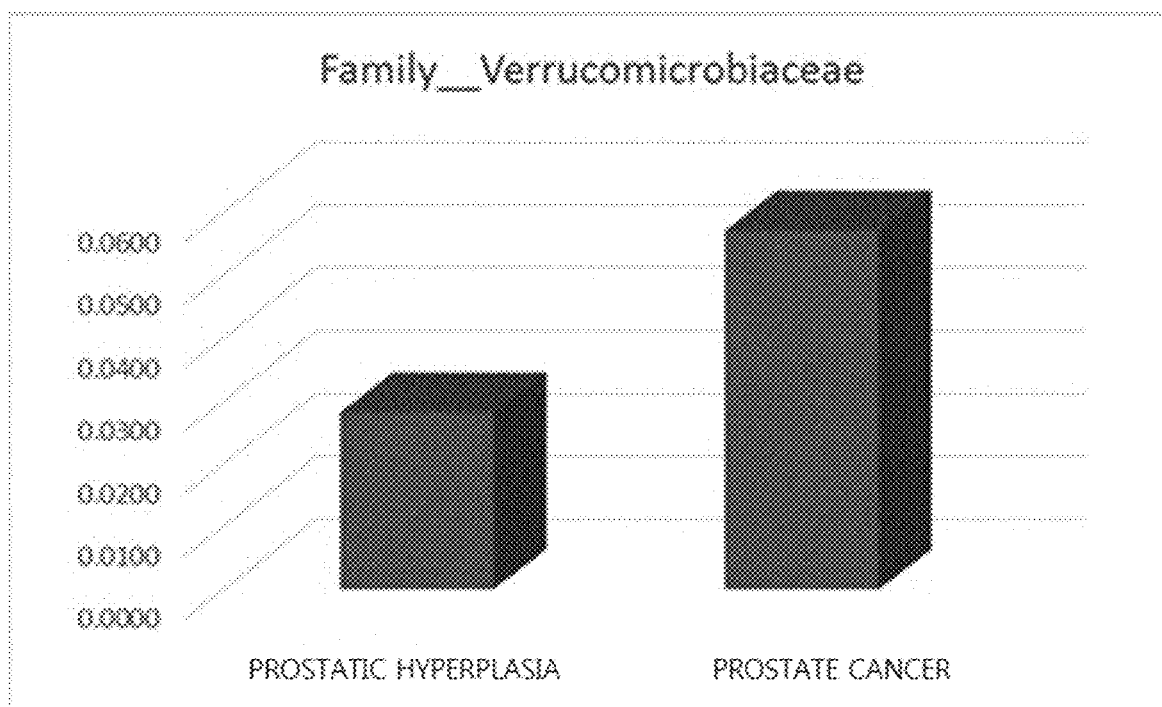
FIG. 10 illustrates distribution results of bacteria-derived EVs exhibiting significant diagnostic performance at a family level, after metagenomic analysis of bacteria-derived EVs isolated from prostate cancer patient-derived urine and prostatic hyperplasia patient-derived urine.
Figure 10:
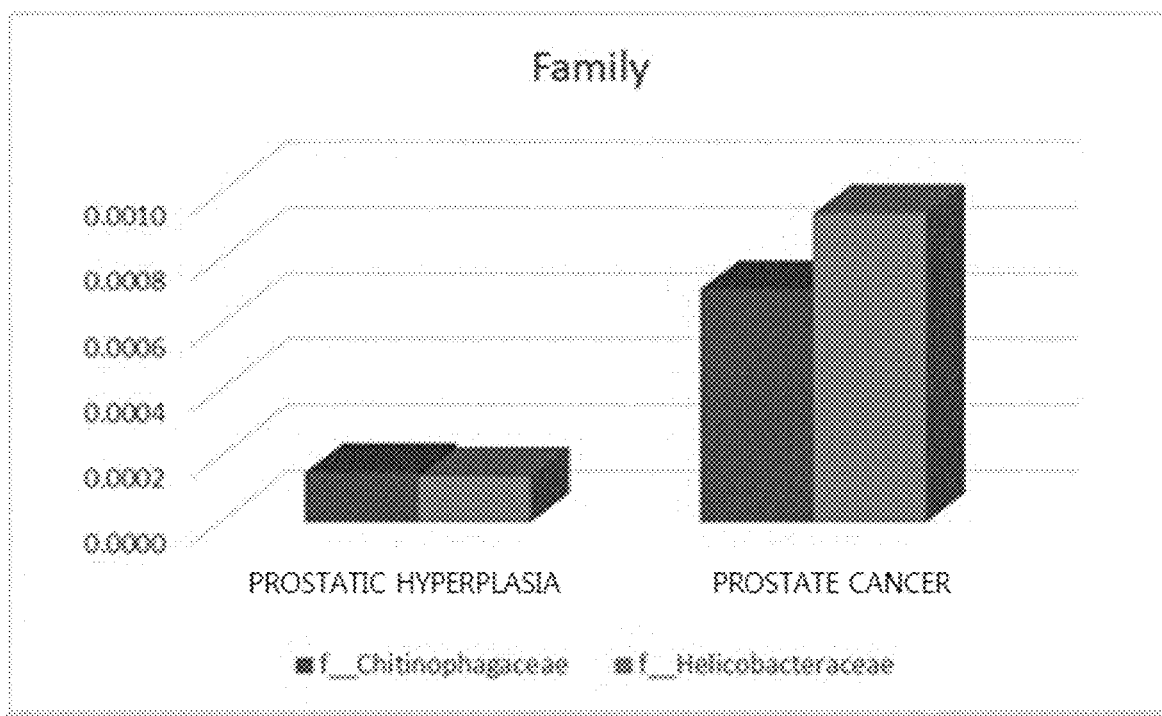

As a result of analyzing bacteria-derived extracellular vesicles in urine at a family level, a diagnostic model developed using, as a biomarker, one or more bacteria from the family Verrucomicrobiaceae, the family Chitinophagaceae, and the family Helicobacteraceae exhibited significant diagnostic performance for prostate cancer (see Table 10 and FIG. 10).

TABLE 10

| Taxon | Prostatic Hyperplasia | | Prostate Cancer | | t-test | | | | |
|---|---|---|---|---|---|---|---|---|---|
| | Mean | SD | Mean | SD | p-value | Ratio | AUC | sensitivity | specificity |
| f__Verrucomicrobiaceae | 0.0281 | 0.0405 | 0.0570 | 0.0561 | 0.0028 | 2.03 | 0.85 | 0.82 | 0.83 |
| f__Chitinophagaceae | 0.0002 | 0.0005 | 0.0007 | 0.0010 | 0.0007 | 4.70 | 0.84 | 0.76 | 0.79 |
| f__Helicobacteraceae | 0.0001 | 0.0005 | 0.0009 | 0.0020 | 0.0070 | 6.76 | 0.83 | 0.73 | 0.79 |

Figure 11:
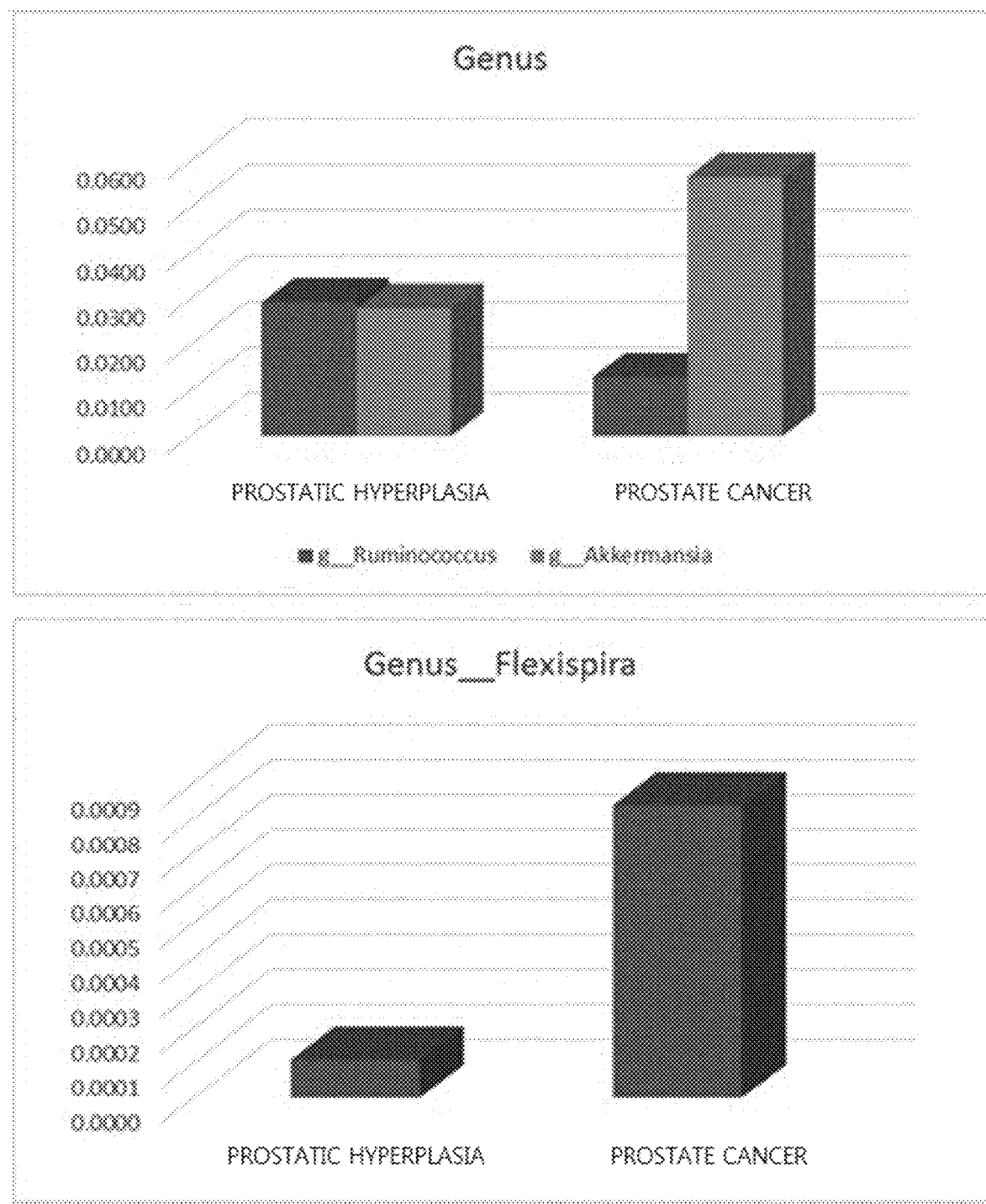
FIG. 11 illustrates distribution results of bacteria-derived EVs exhibiting significant diagnostic performance at a genus level, after metagenomic analysis of bacteria-derived EVs isolated from prostate cancer patient-derived urine and prostatic hyperplasia patient-derived urine.

As a result of analyzing bacteria-derived extracellular vesicles in urine at a genus level, a diagnostic model developed using, as a biomarker, one or more bacteria from the genus *Ruminococcus*, the genus *Akkermansia*, and the genus *Flexispira* exhibited significant diagnostic performance for prostate cancer (see Table 11 and FIG. 11).

TABLE 11

| Taxon | Prostatic Hyperplasia | | Prostate Cancer | | t-test | | | | |
|---|---|---|---|---|---|---|---|---|---|
| | Mean | SD | Mean | SD | p-value | Ratio | AUC | sensitivity | specificity |
| g__Ruminococcus | 0.0292 | 0.0371 | 0.0129 | 0.0137 | 0.0035 | 0.44 | 0.84 | 0.78 | 0.83 |
| g__Akkermansia | 0.0280 | 0.0404 | 0.0556 | 0.0560 | 0.0031 | 2.02 | 0.85 | 0.82 | 0.83 |
| g__Flexispira | 0.0001 | 0.0004 | 0.0008 | 0.0019 | 0.0084 | 7.71 | 0.83 | 0.73 | 0.79 |

Example 6. Prostatic Hyperplasia Diagnostic Model Based on Metagenomic Analysis of Bacteria-Derived EVs Isolated from Urine of Normal Individuals and Prostatic Hyperplasia Patients EVs were isolated from urine samples of 55 prostate cancer patients and 159 normal individuals, and then metagenomic sequencing was performed thereon using the method of Example 3. For the development of a diagnostic model, first, a strain exhibiting a p value of less than 0.05 between two groups in a t-test and a difference of two-fold or more between two groups was selected, and then an area under curve (AUC), sensitivity, and specificity, which are diagnostic performance indexes, were calculated by logistic regression analysis.

Figure 12:
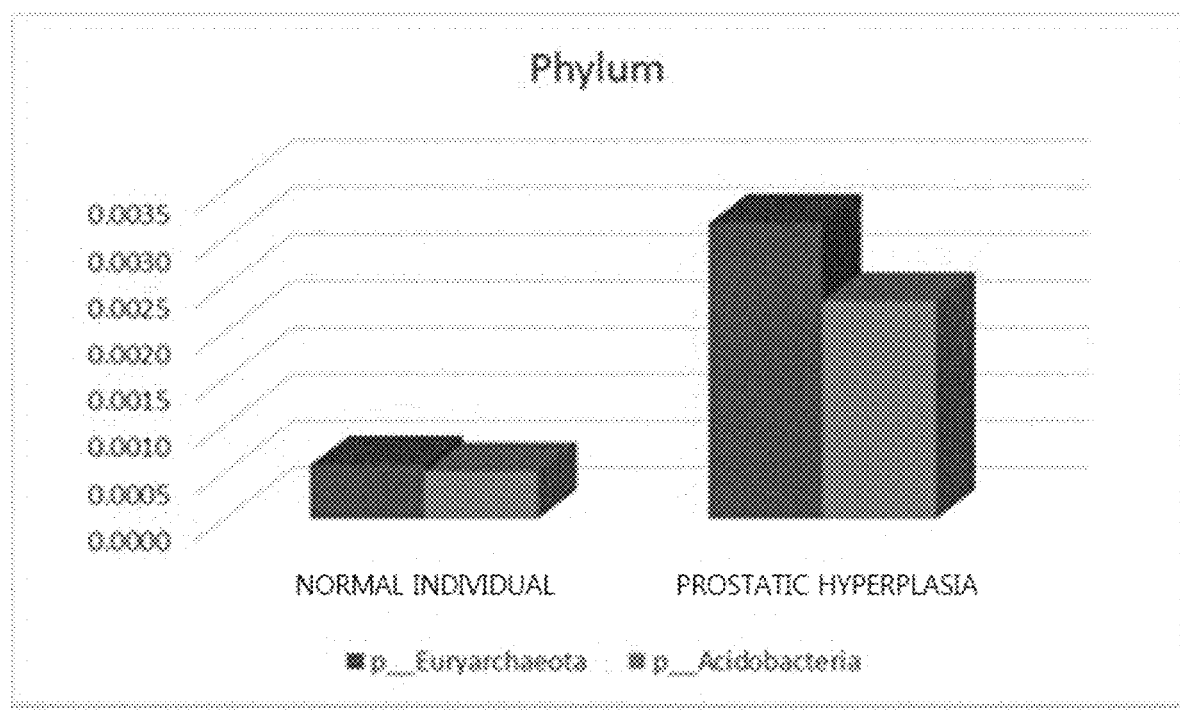
FIG. 12 illustrates distribution results of bacteria-derived EVs exhibiting significant diagnostic performance at a phylum level, after metagenomic analysis of bacteria-derived EVs isolated from prostatic hyperplasia patient-derived urine and normal individual-derived urine.

As a result of analyzing bacteria-derived extracellular vesicles in urine at a phylum level, a diagnostic model developed using, as a biomarker, one or more bacteria from the phylum Euryarchaeota and the phylum Acidobacteria exhibited significant diagnostic performance for prostatic hyperplasia (see Table 12 and FIG. 12).

TABLE 12

| Taxon | Normal Individual | | Prostatic Hyperplasia | | t-test | | | | | |
|---|---|---|---|---|---|---|---|---|---|---|
| | Mean | SD | Mean | SD | p-value | fold | AUC | Accuracy | sensitivity | specificity |
| p__Euryarcheaota | 0.0006 | 0.0013 | 0.0032 | 0.0064 | 0.0044 | 5.50 | 0.69 | 0.77 | 0.96 | 0.20 |
| p__Acidobacteria | 0.0005 | 0.0017 | 0.0023 | 0.0043 | 0.0032 | 4.61 | 0.69 | 0.77 | 0.98 | 0.15 |

Figure 13:
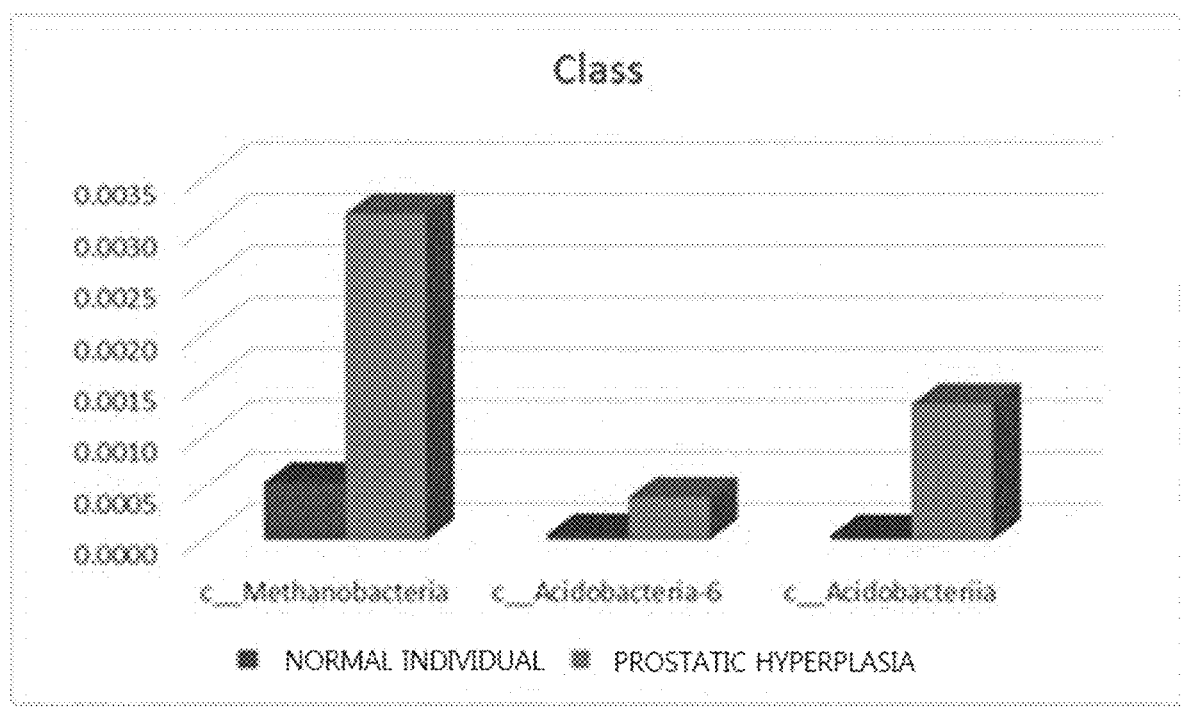
FIG. 13 illustrates distribution results of bacteria-derived EVs exhibiting significant diagnostic performance at a class level, after metagenomic analysis of bacteria-derived EVs isolated from prostatic hyperplasia patient-derived urine and normal individual-derived urine.

As a result of analyzing bacteria-derived extracellular vesicles in urine at a class level, a diagnostic model developed using, as a biomarker, one or more bacteria from the class Methanobacteria, the class Acidobacteria, and the class Acidobacteriia exhibited significant diagnostic performance for prostatic hyperplasia (see Table 13 and FIG. 13).

TABLE 13

| Taxon | Normal Individual | | Prostatic Hyperplasia | | t-test | | | | | |
|---|---|---|---|---|---|---|---|---|---|---|
| | Mean | SD | Mean | SD | p-value | fold | AUC | Accuracy | sensitivity | specificity |
| c__Methanobacteria | 0.0006 | 0.0012 | 0.0032 | 0.0064 | 0.0042 | 5.68 | 0.69 | 0.77 | 0.96 | 0.20 |
| c__Acidobacteria-6 | 0.0001 | 0.0003 | 0.0004 | 0.0009 | 0.0070 | 7.75 | 0.64 | 0.76 | 0.97 | 0.15 |
| c__Acidobacteriia | 0.0000 | 0.0002 | 0.0013 | 0.0029 | 0.0021 | 31.00 | 0.69 | 0.79 | 0.99 | 0.20 |

Figure 14:
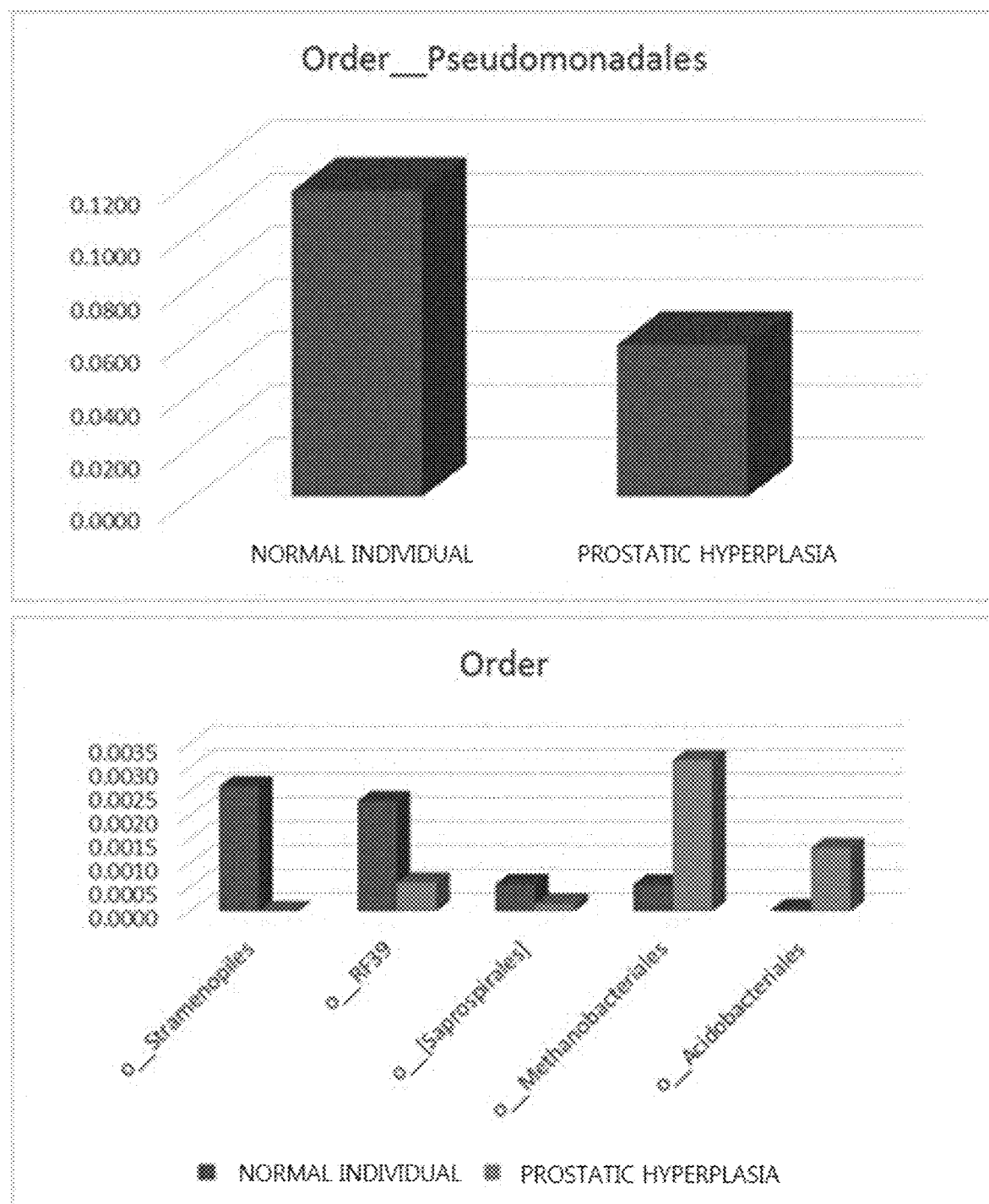
FIG. 14 illustrates distribution results of bacteria-derived EVs exhibiting significant diagnostic performance at an order level, after metagenomic analysis of bacteria-derived EVs isolated from prostatic hyperplasia patient-derived urine and normal individual-derived urine.

As a result of analyzing bacteria-derived extracellular vesicles in urine at an order level, a diagnostic model developed using, as a biomarker, one or more bacteria from the order Stramenopiles, the order RF39, the order Saprospirales, the order Pseudomonadales, the order Methanobacteriales, and the order Acidobacteriales exhibited significant diagnostic performance for prostatic hyperplasia (see Table 14 and FIG. 14).

TABLE 14

| Taxon | Normal Individual | | Prostatic Hyperplasia | | t-test | | | | | |
|---|---|---|---|---|---|---|---|---|---|---|
| | Mean | SD | Mean | SD | p-value | fold | AUC | Accuracy | sensitivity | specificity |
| o__Stramenopiles | 0.0026 | 0.0059 | 0.0000 | 0.0000 | 0.0013 | 0.00 | 0.77 | 0.72 | 0.95 | 0.07 |
| o__RF39 | 0.0023 | 0.0068 | 0.0006 | 0.0012 | 0.0027 | 0.26 | 0.65 | 0.75 | 0.98 | 0.07 |
| o__[Saprospirales] | 0.0006 | 0.0016 | 0.0002 | 0.0005 | 0.0033 | 0.27 | 0.64 | 0.74 | 1.00 | 0.00 |
| o__Pseudomonadales | 0.1154 | 0.1282 | 0.0573 | 0.0344 | 0.0000 | 0.50 | 0.73 | 0.79 | 0.96 | 0.27 |
| o__Methanobacteriales | 0.0006 | 0.0012 | 0.0032 | 0.0064 | 0.0042 | 5.68 | 0.69 | 0.77 | 0.96 | 0.20 |
| o__Acidobacteriales | 0.0000 | 0.0002 | 0.0013 | 0.0029 | 0.0021 | 31.00 | 0.69 | 0.79 | 0.99 | 0.20 |

Figure 15:
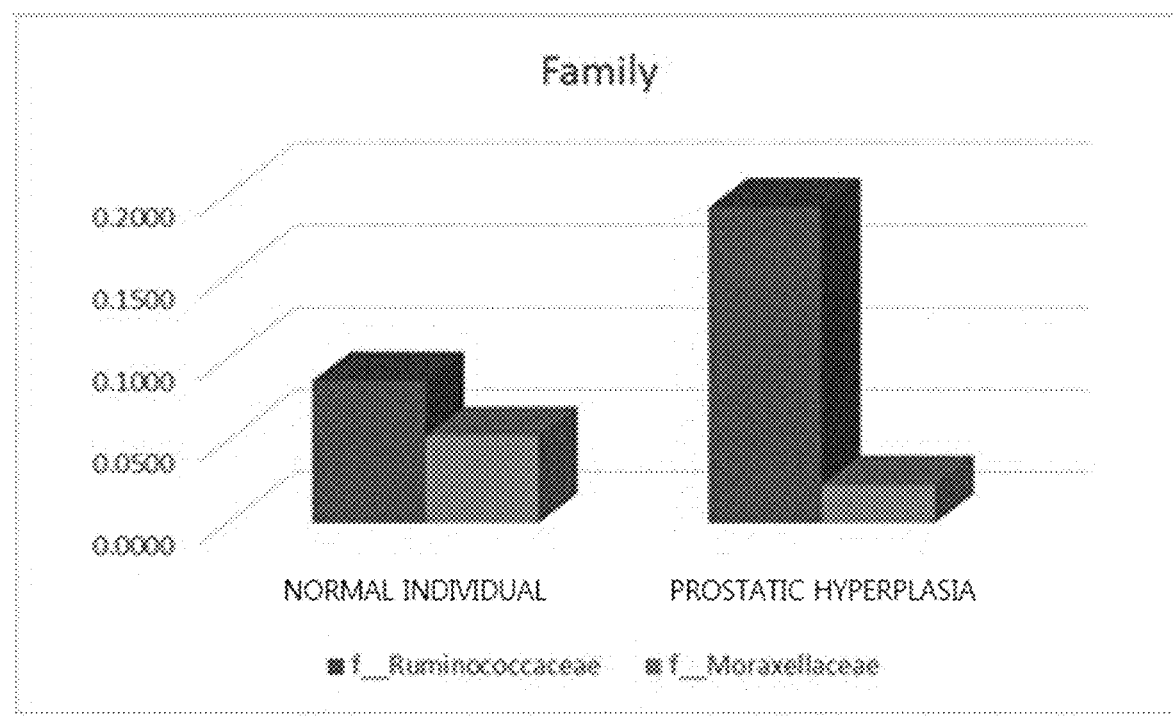
FIG. 15 illustrates distribution results of bacteria-derived EVs exhibiting significant diagnostic performance at a family level, after metagenomic analysis of bacteria-derived EVs isolated from prostatic hyperplasia patient-derived urine and normal individual-derived urine.
Figure 15:
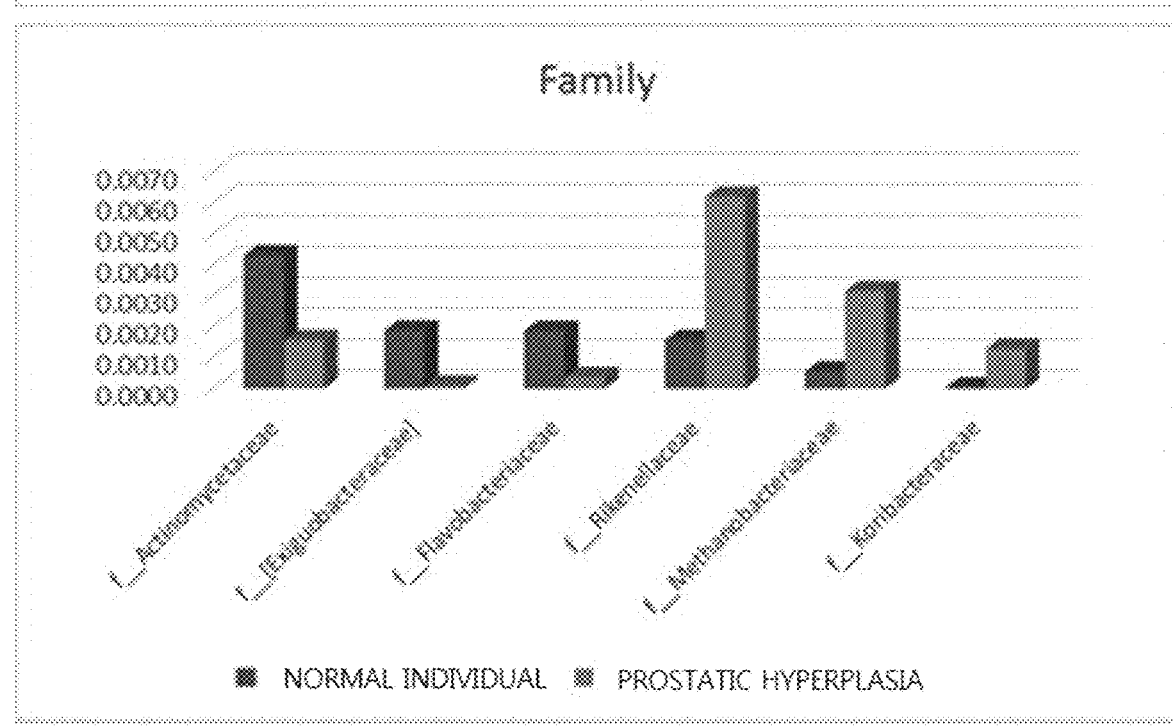

As a result of analyzing bacteria-derived extracellular vesicles in urine at a family level, a diagnostic model developed using, as a biomarker, one or more bacteria from the family Exiguobacteraceae, the family Flavobacteriaceae, the family Actinomycetaceae, the family Moraxellaceae, the family Ruminococcaceae, the family Rikenellaceae, the family Methanobacteriaceae, and the family Koribacteraceae exhibited significant diagnostic performance for prostatic hyperplasia (see Table 15 and FIG. 15).

TABLE 15

| Taxon | Normal Individual | | Prostatic Hyperplasia | | t-test | | | | | |
|---|---|---|---|---|---|---|---|---|---|---|
| | Mean | SD | Mean | SD | p-value | fold | Auc | Accuracy | sensitivity | specificity |
| f__[Exiguobacteraceae] | 0.0019 | 0.0065 | 0.0001 | 0.0003 | 0.0008 | 0.05 | 0.66 | 0.74 | 1.00 | 0.00 |
| f__Flavobacteriaceae | 0.0019 | 0.0030 | 0.0004 | 0.0007 | 0.0000 | 0.20 | 0.70 | 0.75 | 0.99 | 0.05 |
| f__Actinomycetaceae | 0.0043 | 0.0102 | 0.0016 | 0.0020 | 0.0016 | 0.36 | 0.67 | 0.75 | 1.00 | 0.02 |
| f__Moraxellaceae | 0.0532 | 0.0884 | 0.0231 | 0.0187 | 0.0001 | 0.43 | 0.69 | 0.75 | 0.97 | 0.11 |
| f__Ruminococcaceae | 0.0867 | 0.0797 | 0.1921 | 0.1608 | 0.0000 | 2.22 | 0.75 | 0.80 | 0.98 | 0.27 |
| f__Rikenellaceae | 0.0016 | 0.0026 | 0.0062 | 0.0079 | 0.0001 | 3.97 | 0.79 | 0.79 | 0.96 | 0.31 |
| f__Methanobacteriaceae | 0.0006 | 0.0012 | 0.0032 | 0.0064 | 0.0042 | 5.68 | 0.69 | 0.77 | 0.96 | 0.20 |
| f__Koribacteraceae | 0.0000 | 0.0002 | 0.0013 | 0.0029 | 0.0022 | 40.87 | 0.69 | 0.79 | 0.99 | 0.20 |

Figure 16:
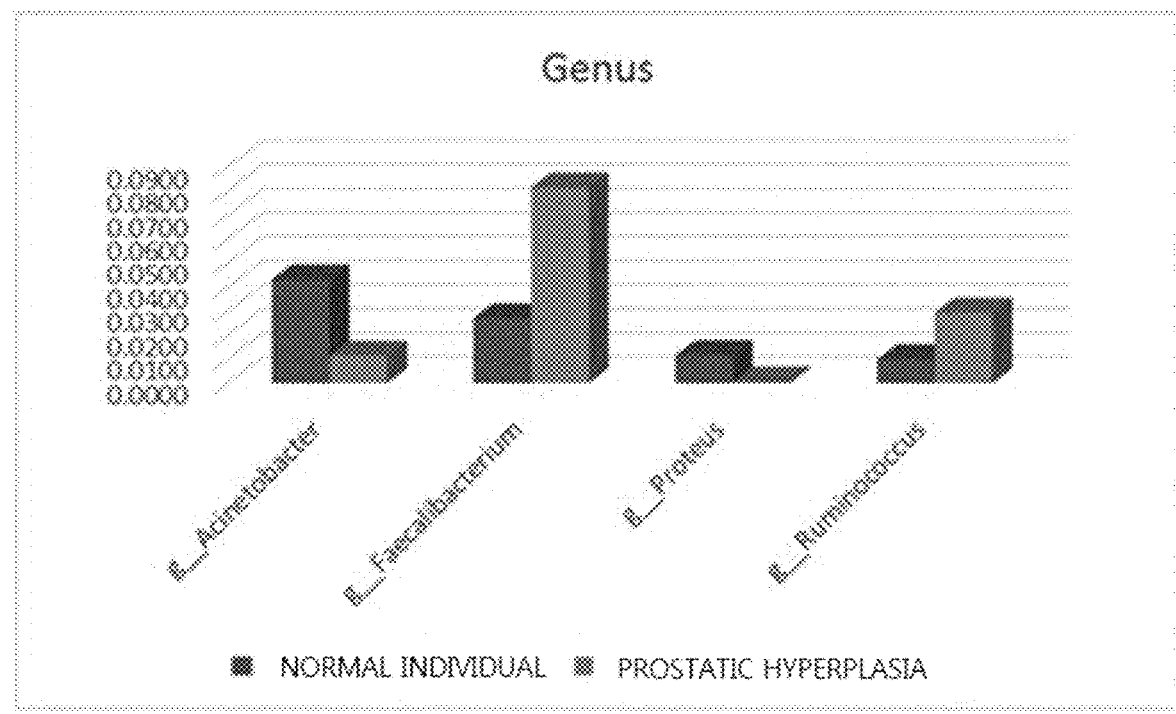
FIG. 16 illustrates distribution results of bacteria-derived EVs exhibiting significant diagnostic performance at a genus level, after metagenomic analysis of bacteria-derived EVs isolated from prostatic hyperplasia patient-derived urine and normal individual-derived urine.
Figure 16:
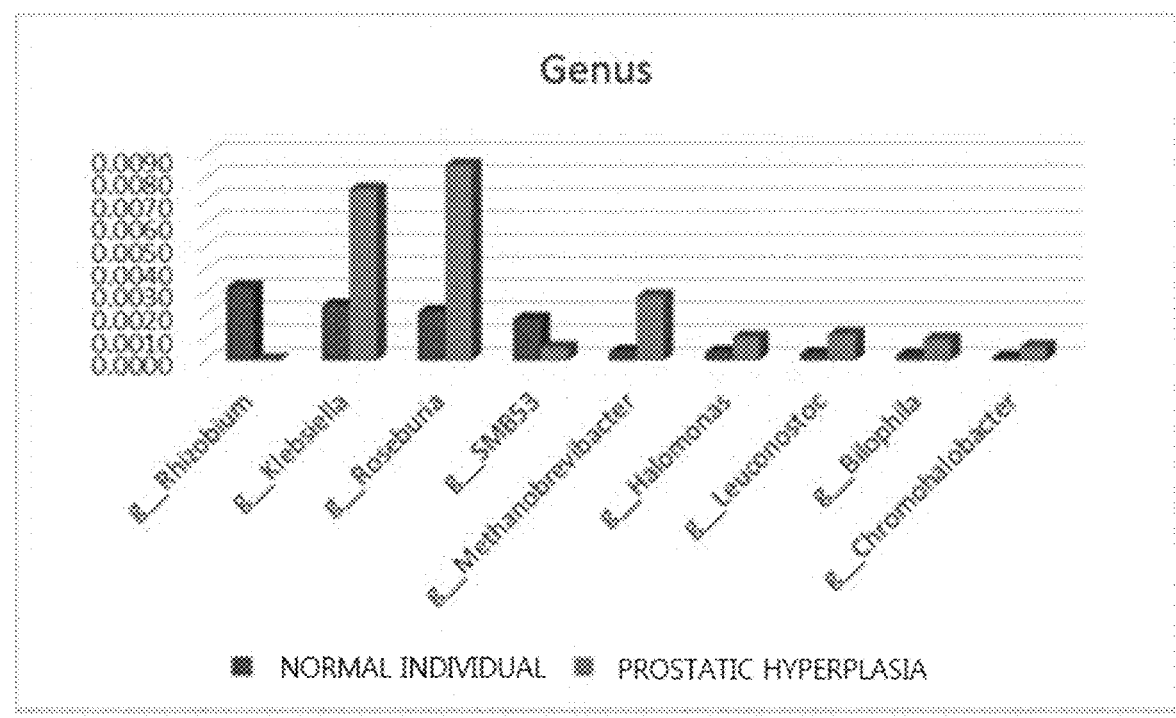

As a result of analyzing bacteria-derived extracellular vesicles in urine at a genus level, a diagnostic model developed using, as a biomarker, one or more bacteria from the genus Rhizobium, the genus Proteus, the genus Acinetobacter, the genus SMB53, the genus Halomonas, the genus Ruminococcus, the genus Faecalibacterium, the genus Klebsiella, the genus Roseburia, the genus Leuconostoc, the genus Bilophila, the genus Chromohalobacter, and the genus Methanobrevibacter exhibited significant diagnostic performance for prostatic hyperplasia (see Table 16 and FIG. 16).

TABLE 16

| Taxon | Normal Individual | | Prostatic Hyperplasia | | t-test | | | | | |
|---|---|---|---|---|---|---|---|---|---|---|
| | Mean | SD | Mean | SD | p-value | fold | Auc | Accuracy | sensitivity | specificity |
| g__Rhizobium | 0.0032 | 0.0050 | 0.0000 | 0.0000 | 0.0000 | 0.00 | 0.92 | 0.89 | 0.97 | 0.67 |
| g__Proteus | 0.0115 | 0.0202 | 0.0006 | 0.0010 | 0.0000 | 0.05 | 0.83 | 0.79 | 0.93 | 0.36 |
| g__Acinetobacter | 0.0431 | 0.0871 | 0.0113 | 0.0086 | 0.0000 | 0.26 | 0.71 | 0.75 | 0.96 | 0.15 |
| g__SMB53 | 0.0018 | 0.0029 | 0.0005 | 0.0007 | 0.0000 | 0.30 | 0.70 | 0.75 | 0.97 | 0.11 |
| g__Halomonas | 0.0003 | 0.0007 | 0.0010 | 0.0016 | 0.0050 | 2.90 | 0.68 | 0.76 | 0.97 | 0.16 |
| g__Ruminococcus | 0.0098 | 0.0156 | 0.0292 | 0.0371 | 0.0004 | 2.98 | 0.69 | 0.78 | 0.98 | 0.20 |
| g__Faecalibacterium | 0.0269 | 0.0355 | 0.0813 | 0.0841 | 0.0000 | 3.02 | 0.73 | 0.81 | 0.99 | 0.31 |
| g__Klebsialla | 0.0024 | 0.0046 | 0.0075 | 0.0086 | 0.0001 | 3.14 | 0.80 | 0.78 | 0.96 | 0.25 |
| g__Roseburia | 0.0021 | 0.0040 | 0.0085 | 0.0085 | 0.0000 | 4.04 | 0.81 | 0.79 | 0.94 | 0.35 |
| g__Leuconostoc | 0.0003 | 0.0007 | 0.0011 | 0.0019 | 0.0017 | 4.28 | 0.68 | 0.78 | 0.98 | 0.20 |
| g__Bilphila | 0.0002 | 0.0008 | 0.0009 | 0.0018 | 0.0064 | 4.29 | 0.70 | 0.77 | 0.99 | 0.13 |
| g__Chromohalobacter | 0.0001 | 0.0006 | 0.0006 | 0.0012 | 0.0066 | 5.06 | 0.67 | 0.77 | 0.99 | 0.13 |
| g__Methanobrevibacter | 0.0004 | 0.0009 | 0.0028 | 0.0063 | 0.0067 | 7.55 | 0.68 | 0.78 | 0.96 | 0.25 |

The above description of the present invention is provided only for illustrative purposes, and it will be understood by one of ordinary skill in the art to which the present invention pertains that the invention may be embodied in various modified forms without departing from the spirit or essential characteristics thereof. Thus, the embodiments described herein should be considered in an illustrative sense only and not for the purpose of limitation.

INDUSTRIAL APPLICABILITY

According to the present invention, a risk for prostate cancer and prostatic hyperplasia can be predicted through metagenomic analysis of genes present in bacteria-derived extracellular vesicles using a human body-derived sample, and thus the onset of prostatic diseases can be delayed or prostatic diseases can be prevented through appropriate management by early diagnosis and prediction of a risk group for a prostatic disease, and, even after prostatic hyperplasia or prostate cancer occurs, early diagnosis therefor can be implemented, thereby lowering the incidence rate of a prostatic disease and increasing therapeutic effects.

The invention claimed is:

1. A method for diagnosing an increased risk of prostate cancer or prostatic hyperplasia comprising:
(a) obtaining a urine sample from a subject;
(b) isolating extracellular vesicles (EVs) from the urine sample;
(c) extracting DNA from the EVs;
(d) performing a polymerase chain reaction (PCR) on the extracted DNA using a first primer set forth in SEQ ID NO: 1 and a second primer set forth in SEQ ID NO: 2 to produce PCR products;
(e) sequencing the PCR products;
(f) analyzing the sequenced PCR products to determine the identity of the bacteria from which the EVs were derived and the and quantity of the bacteria-derived EVs; and
(g-1) diagnosing prostate cancer by detecting an increase or decrease in the quantity of bacteria-derived EVs by two-fold or more in the urine sample of the subject as compared to that in samples obtained from normal, control individuals, or
(g-2) diagnosing prostate cancer by detecting an increase or decrease in the quantity of bacteria-derived EVs by two-fold or more in the urine sample of the subject as compared to that in samples obtained from control patients having prostatic hyperplasia, or
(g-3) diagnosing prostatic hyperplasia by detecting an increase or decrease in the quantity of bacteria-derived EVs by two-fold or more in the urine sample of the subject as compared to that in samples obtained from normal, control individuals,
wherein:
(i) in (g-1),
the EVs are derived from one or more bacteria selected from the group consisting of: the genus *Rhizobium*, the genus *Tetragenococcus*, the genus *Proteus*, the genus *Morganella*, the genus *Exiguobacterium*, the genus *Oribacterium*, the genus *Porphyromonas*, the genus *Actinomyces*, the genus *Cellulomonas*, the genus *Jeotgalicoccus*, the genus *Acinetobacter*, the genus *Fusobacterium*, the genus *Enterobacter*, the genus *Neisseria*, the genus *Adlercreutzia*, the genus SMB53, the genus *Parabacteroides*, the genus *Faecalibacterium*, the genus *Catenibacterium*, the genus *Roseburia*, the genus *Akkermansia*, the genus *Methanobrevibacter*, the genus *Clostridium*, the genus *Klebsiella*, the genus *Chryseobacterium*, the genus *Halomonas*, the genus *Aggregatibacter*, the genus *Rhodoplanes*, the genus *Thermoanaerobacterium*, the genus *Candidatus Koribacter*, and the genus *Flexispira*,
the increase in the quantity of bacteria-derived EVs by two-fold or more is in the EVs derived from the bacteria consisting of the genus *Faecalibacterium*, the genus *Catenibacterium*, the genus *Roseburia*, the genus *Akkermansia*, the genus *Methanobrevibacter*, the genus *Clostridium*, the genus *Klebsiella*, the genus *Chryseobacterium*, the genus *Halomonas*, the genus *Aggregatibacter*, the genus *Rhodoplanes*, the genus *Thermoanaerobacterium*, the genus *Candidatus Koribacter*, and the genus *Flexispira*, and
the decrease in the quantity of bacteria-derived EVs by two-fold or more is in the EVs derived from the bacteria consisting of the genus *Rhizobium*, the genus *Tetragenococcus*, the genus *Proteus*, the genus *Morganella*, the genus *Exiguobacterium*, the genus *Oribacterium*, the genus *Porphyromonas*, the genus *Actinomyces*, the genus *Cellulomonas*, the genus *Jeotgalicoccus*, the genus *Acinetobacter*, the genus *Fusobacterium*, the genus *Enterobacter*, the genus *Neisseria*, the genus *Adlercreutzia*, the genus SMB53, and the genus *Parabacteroides*;
(ii) in (g-2),
the EVs are derived from one or more bacteria selected from the group consisting of: the genus *Ruminococcus*, the genus *Akkermansia*, and the genus *Flexispira*, the increase in the quantity of bacteria-derived EVs by two-fold or more is in the EVs derived from the bacteria consisting of the genus *Akkermansia* and the genus *Flexispira*, and the decrease in the quantity of bacteria-derived EVs by two-fold or more is in the EVs derived from the genus *Ruminococcus*; and (iii) in (g-3), the EVs are derived from one or more bacteria selected from the group consisting of: the genus *Rhizobium*, the genus *Proteus*, the genus *Acinetobacter*, the genus SMB53, the genus *Halomonas*, the genus *Ruminococcus*, the genus *Faecalibacterium*, the genus *Klebsiella*, the genus *Roseburia*, the genus *Leuconostoc*, the genus *Bilophila*, the genus *Chromohalobacter*, and the genus *Methanobrevibacter*, the increase in the quantity of bacteria-derived EVs by two-fold or more is in the EVs derived from the bacteria consisting of the genus *Halomonas*, the genus *Ruminococcus*, the genus *Faecalibacterium*, the genus *Klebsiella*, the genus *Roseburia*, the genus *Leuconostoc*, the genus *Bilophila*, the genus *Chromohalobacter*, and the genus *Methanobrevibacter*, and the decrease in the quantity of bacteria-derived EVs by two-fold or more is in the EVs derived from the genus *Rhizobium*, the genus *Proteus*, the genus *Acinetobacter*, and the genus SMB53.

* * * * *